United States Patent
Brown et al.

(10) Patent No.: US 7,025,986 B2
(45) Date of Patent: Apr. 11, 2006

(54) MICROMESH INTERPROXIMAL DEVICES

(75) Inventors: Dale G. Brown, Wharton, TX (US); Ira D. Hill, Locust, NJ (US)

(73) Assignee: International Tape Partners LLC, Stafford, TX (US)

( * ) Notice: Subject to any disclaimer, the term of this patent is extended or adjusted under 35 U.S.C. 154(b) by 534 days.

(21) Appl. No.: 10/073,682

(22) Filed: Feb. 11, 2002

(65) Prior Publication Data

US 2003/0178044 A1   Sep. 25, 2003

(51) Int. Cl.
*A61K 9/70* (2006.01)
*A61F 13/00* (2006.01)

(52) U.S. Cl. .............. 424/443; 424/401; 424/405

(58) Field of Classification Search ............ 424/49, 424/401, 405, 443, 52
See application file for complete search history.

(56) References Cited

U.S. PATENT DOCUMENTS

| | | | |
|---|---|---|---|
| 2,185,789 A | 1/1940 | Jacque | 18/54 |
| 2,667,443 A | 1/1954 | Ashton | 167/93 |
| 2,772,205 A | 11/1956 | King | 167/93 |
| 2,954,587 A | 10/1960 | Rasmussen | 18/47.5 |
| 3,214,899 A | 11/1965 | Wininger, Jr. et al. | 57/140 |
| 3,662,930 A | 5/1972 | Meierhoefer | 222/564 |
| 3,693,851 A | 9/1972 | Yazawa | 225/3 |
| 3,699,979 A | 10/1972 | Muhler et al. | 132/89 |
| 3,800,812 A | 4/1974 | Jaffe | 132/89 |
| 3,838,702 A | 10/1974 | Standish et al. | 132/89 |
| 3,897,795 A | 8/1975 | Engel | 132/89 |
| 3,928,618 A | 12/1975 | Bauman | 424/311 |
| 3,943,949 A | 3/1976 | Ashton et al. | 132/89 |
| 4,029,113 A | 6/1977 | Guyton | 132/91 |
| 4,033,365 A | 7/1977 | Klepak et al. | 132/89 |
| 4,414,990 A | 11/1983 | Yost | 132/91 |
| 4,627,975 A | 12/1986 | Lynch | 424/49 |
| 4,638,823 A | 1/1987 | Newman et al. | 132/91 |
| 4,776,358 A | 10/1988 | Lorch | 132/321 |
| 4,879,076 A | 11/1989 | Sano et al. | 264/28 |
| 4,911,927 A | 3/1990 | Hill et al. | 424/443 |
| 4,950,479 A | 8/1990 | Hill et al. | 424/49 |
| 4,974,615 A | 12/1990 | Doundoulakis | 132/321 |
| 4,986,288 A | 1/1991 | Kent et al. | 132/321 |
| 4,996,011 A | 2/1991 | Sano et al. | 264/28 |
| 4,998,011 A | 3/1991 | Shuman | 250/201.5 |
| 5,002,714 A | 3/1991 | Sano et al. | 264/119 |
| 5,032,387 A | 7/1991 | Hill et al. | 424/49 |
| 5,033,365 A | 7/1991 | Rao et al. | 99/349 |
| 5,033,488 A | 7/1991 | Curtis et al. | 132/321 |
| 5,091,133 A | 2/1992 | Kobayashi et al. | 264/119 |
| 5,098,711 A * | 3/1992 | Hill et al. | 424/401 |
| 5,106,555 A | 4/1992 | Kobayashi et al. | 264/112 |
| 5,106,558 A | 4/1992 | Kobayashi et al. | 264/119 |
| 5,165,713 A | 11/1992 | Picard | 280/433 |
| 5,165,913 A | 11/1992 | Hill et al. | 424/49 |
| 5,200,129 A | 4/1993 | Kobayashi et al. | 264/119 |
| 5,209,251 A | 5/1993 | Curtis et al. | 132/321 |
| 5,220,932 A | 6/1993 | Blass | 132/321 |
| 5,357,990 A | 10/1994 | Suhonen et al. | 132/321 |

(Continued)

*Primary Examiner*—Thurman K. Page
*Assistant Examiner*—Micah-Paul Young

(57) ABSTRACT

A shred resistant, ultra-high molecular weight polyethylene, micromesh interproximal device produced by fibrillating and slitting stretched polyethylene film having a tensile-strength from between about 0.7 GPa and about 5 GPa, where said polyethylene has an intrinsic viscosity of from between about 5 and about 50 dl/g and wherein said resultant micromesh tape is coated with an oral care substance at from between about 10 and about 120 mg/yd.

22 Claims, 20 Drawing Sheets

U.S. PATENT DOCUMENTS

| | | | |
|---|---|---|---|
| 5,423,337 A | 6/1995 | Ahlert et al. | 132/321 |
| 5,433,226 A | 7/1995 | Burch | 132/321 |
| 5,479,952 A * | 1/1996 | Zachariades et al. | 132/321 |
| 5,503,842 A | 4/1996 | Fazan et al. | 424/443 |
| 5,518,012 A | 5/1996 | Dolan et al. | 132/321 |
| 5,538,667 A | 7/1996 | Hill et al. | 252/312 |
| 5,558,901 A | 9/1996 | Gilligan et al. | 427/2.29 |
| 5,561,959 A | 10/1996 | Alderman et al. | 52/407.3 |
| 5,578,373 A | 11/1996 | Kobayashi et al. | 428/364 |
| 5,598,373 A | 1/1997 | Wada et al. | 365/230.03 |
| RE35,439 E | 2/1997 | Rosenberger | 132/321 |
| 5,603,921 A | 2/1997 | Bowen | 424/49 |
| 5,645,841 A | 7/1997 | Hill et al. | 424/401 |
| 5,665,374 A | 9/1997 | Hill et al. | 424/435 |
| 5,693,708 A | 12/1997 | Iwanami et al. | 524/585 |
| 5,695,708 A | 12/1997 | Karp et al. | 264/401 |
| 5,702,657 A | 12/1997 | Yoshida et al. | 264/112 |
| 5,711,935 A | 1/1998 | Hill et al. | 424/49 |
| 5,718,251 A | 2/1998 | Gray et al. | 132/321 |
| 5,723,388 A | 3/1998 | Kobayashi et al. | 442/170 |
| 5,755,243 A | 5/1998 | Roberts et al. | 132/321 |
| 5,760,117 A | 6/1998 | Chen | 524/270 |
| 5,765,576 A | 6/1998 | Dolan et al. | 132/321 |
| 5,787,758 A | 8/1998 | Sheldon | 74/790.07 |
| 5,830,495 A | 11/1998 | Ochs | 424/443 |
| 5,845,652 A | 12/1998 | Tseng et al. | 132/200 |
| 5,848,600 A | 12/1998 | Bacino et al. | 132/321 |
| 5,884,639 A | 3/1999 | Chen | 132/321 |
| 5,911,228 A | 6/1999 | Curtis et al. | 132/321 |
| 5,918,609 A | 7/1999 | Tsao et al. | 132/321 |
| 5,962,572 A | 10/1999 | Chen | 524/474 |
| 5,998,431 A | 12/1999 | Tseng et al. | 514/300 |
| 6,003,525 A | 12/1999 | Katz | 132/321 |
| 6,017,480 A | 1/2000 | Yoshida et al. | 264/216 |
| 6,027,593 A | 2/2000 | Lunt et al. | 156/167 |
| 6,080,481 A | 6/2000 | Ochs et al. | 428/372 |
| 6,083,208 A | 7/2000 | Modak et al. | 604/265 |
| 6,148,830 A | 11/2000 | Chen | 132/321 |
| 6,161,555 A | 12/2000 | Chen | 132/321 |

* cited by examiner

UNCOATED MICROMESH

UNCOATED MICROMESH

UNCOATED MICROMESH

UNCOATED MONOFILAMENT TAPE

UNCOATED MULTIFILAMENT DENTAL FLOSS

MICROMESH COATED

MICROMESH COATED

MICROMESH UNCOATED

MICROMESH COATED

MICROMESH COATED

MICROMESH INTERPROXIMAL DEVICES

FIELD OF THE INVENTION

The present invention relates to coated interproximal devices produced from ultra-high molecular weight, polyethylene film that has been stretched, fibrillated and slit, to produce a micromesh, honeycomb or web-type tape structure distinct from multifilament and monofilament interproximal devices, wherein this micromesh tape is coated with an oral care substance which, during flossing, releases said coating while demonstrating ultra-shred resistance and the capacity to entrap and remove loosened debris from interproximal and subgingival areas.

BACKGROUND OF THE INVENTION

Proper use of dental floss is necessary to clean the considerable area on the interproximal surfaces of teeth which cannot be reached by the bristles of a toothbrush.

The purpose of dental floss is:

1. to dislodge and remove any decomposing food material that has accumulated at the interproximal surfaces that cannot be removed by brushing, and
2. to dislodge and remove as much as possible the growth of bacterial biofilm (plaque) upon the teeth or the superimposed calculus that has accumulated there since the previous cleaning.

The concept of the use of dental floss for cleansing interproximal spaces appears to have been introduced by Parmly in 1819 ("Practical Guide to the Management of the Teeth"," Collins & Croft, Philadelphia Pa.). Parmly suggested the use of waxed silk to clean teeth of persons subject to gingival inflammation. Numerous types of floss were developed and used for cleaning, until finally in 1948 Bass established the optimum characteristics of dental floss [*Dental Items of Interest*, 70, 921–34, (1948)].

Surprisingly, multifilament and monofilament floss marketers have ignored Bass for the past 50 plus years. Bass warned that dental floss treated with sizing, binders and/or wax produces a "cord" effect that reduces flossing efficiency dramatically. Almost all multifilament floss sold today including unwaxed floss contains binders and/or sizing substances. These "sticky" substances are used to keep the floss twists from falling off a spool during dispensing by holding the floss together.

Additionally, most multifilament floss sold at retail today is also "waxed" to assist penetration to interproximal regions. The resulting "cord" effect described by Bass often makes the floss bundle difficult to force between closely spaced teeth.

The optimum characteristics of dental floss as described by Bass in 1948 have been ignored by most interproximal device manufacturers. Specifically, Bass suggests that these waxed and sized flosses produce an undesirable "cord" effect as discussed above as distinguished from the desirable "spread effect" of unwaxed, unsized floss which flattens out and widens, with the filaments spread out. The potential for separate mechanical action of spread out filaments is nullified by this "cord" effect. Also sacrificed are the spaces between the filaments, which according to Bass are necessary to receive, hold and remove the microscopic material dislodged during flossing. Thus, the mechanical cleaning attributed to spread filaments and essentially all of the evacuation of microscopic materials from the interproximal spaces by entrapment by these spread-out filaments is impaired or sacrificed with waxed and/or sized flosses, as well as with monofilament tapes, because of this "cord" effect.

It is not surprising that shred resistance has been the basic claim of several dental tape marketers. The introduction of Gore's Glide®, with its monofilament construction, was proposed as the ultimate shred resistant floss. Historically, the typical response to shredding was to develop a "tighter" bonded and smaller diameter floss that did not spread out and did not shred. It is not difficult to see how the "ultimate cord", i.e. monofilament tape construction, evolved from this approach. Clearly, the monofilament floss is easier to use than traditional bonded multifilament flosses, because of this no-shredding feature. However, shred resistance is achieved with a sacrifice in entrapment and removal of material dislodged during flossing.

It is generally accepted that floss is not a "user-friendly" product, i.e. it is difficult to do. It causes pain and bleeding and it results in a bad taste in the mouth. Most market researchers agree that anything that can be done to make flossing more positive should be implemented to encourage more frequent flossing and more wide spread floss use. The addition to floss of various coatings including those: saliva-soluble, crystal-free coatings of the present invention which contain chemotherapeutic ingredients, mouth conditioning substances such as silicones, cleaners and Soft Abrasives™ that leave a "clean, just brushed feeling" as taught by the present invention are all sources of positive feed back to the flosser that would be considered encouraging and supportive. To achieve these advances requires basic changes in floss construction and in physical chemistry of floss additives as well as coating technology that avoids the "cord" effect characteristic of waxed floss and monofilament tape and is particularly responsive to the need for entrapment and removal of material dislodged during flossing.

Shred-resistant monofilament interproximal devices are described and claimed in U.S. Pat. No. Re 35,439; 3,800,812; 4,974,615; 5,760,117; 5,433,226; 5,479,952; 5,503,842; 5,755,243; 5,845,652; 5,884,639; 5,918,609; 5,962,572; 5,998,431; 6,003,525; 6,083,208; 6,148,830; 6,161,555 and 6,027,592. These monofilament dental tapes generally have serious shortcomings in: gentleness, delivering coatings during flossing, being handled easily and conveniently during flossing and entrapping and removing material dislodged during flossing.

Shred-resistant, polytetrafluoroethylene (PTFE) based monofilament interproximal devices are described in: U.S. Pat. Nos. 5,209,251; 5,033,488; 5,518,012; 5,911,228; 5,220,932; 4,776,358; 5,718,251; 5,848,600; 5,787,758 and 5,765,576. To date, no commercial versions of these monofilament tapes have been coated effectively, nor can they be used to deliver active ingredients, interproximally and subgingivally during flossing, nor can monofilament tapes entrap and remove materials from interproximal spaces. Handling during flossing is difficult. Most have to be folded to provide a consumer acceptable edge. Many are plagued with serious dimensional inconsistency problems, as well.

Multifilament, interproximal devices are described and claimed in U.S. Pat. Nos. 5,033,365; 3,943,949; 6,080,481; 5,830,495; 2,667,443; 4,638,823; 4,029,113; 2,772,205; 4,627,975; 4,414,990; 3,699,979; 3,897,795; 3,838,702; 4,776,358; 5,718,251; 5,603,921; 5,558,901; 5,423,337; 5,357,990; 4,986,288; 3,897,795; 3,928,618; 5,433,226 and 4,033,365. Most of these flosses would not be classified as shred resistant.

The Hill, et al., patents, namely U.S. Pat. Nos. 4,911,927; 5,098,711; 5,165,913 and 5,711,935, describe compression loaded multifilament flosses. All multifilament interproximal devices pose major consumer problems in the areas of shredding, breaking, etc., with the texturized multifilament dental flosses exhibiting even greater shredding and breaking shortcomings. It is these shortcomings of the multifilament flosses in general that were instrumental in the commercial success of shred-resistant PTFE and other monofilament devices.

The production of ultra-high molecular weight, stretched polyethylene film that has been slit into various tapes of varying width and thickness, which is then fibrillated, i.e. penetrated with various cutting means, to produce these micromesh tapes suitable for compression loading to produce interproximal devices of the present invention is described and claimed in U.S. Pat. Nos. 4,879,076; 4,998,011; 5,002,714; 5,091,133; 5,106,555; 5,106,558; 5,200,129; 5,598,373; 5,693,708 and 5,723,388. Specific methods of fibrillating films are described in U.S. Pat. Nos. 2,185,789; 3,214,899; 2,954,587; 3,662,930 and 3,693,851 and Japanese Patent Publication Nos. 13116/1961 and 16909/1968. Suitable fibrillating tools include fibrillating rollers, various needle bars, separating cones, needle rings and ceramic blades and are available from Burckhardt AG, Basel, Switzerland. Particularly preferred fibrillating tools for producing the micromesh interproximal tapes suitable for coating according to the present invention include: needle bars, tapping screw-like fibrillators or file-like fibrillators. The latter two are illustrated in FIGS. 3 and 4 of the drawings. The fibrillator illustrated in FIG. 4, described as a file-like fibrillator, is the subject of Japanese Utility Model No. 38980/1976.

All of the foregoing references are hereby incorporated by reference.

Effective oral hygiene requires that three control elements be maintained by the individual:

Physical removal of stains, plaque (biofilm) and tartar. This is accomplished in the strongest sense by scraping and abrasion in the dentist's office. Self administered procedures are required frequently between visits and range from tooth brushing with an appropriate abrasive toothpaste, through flossing and water jet action, down to certain abrasive foods and even the action of the tongue against the tooth surface.

Surfactant Cleansing, where the source of the surfactant is generally: toothpaste, mouth rinse and/or dental floss. This is required to remove: food debris and staining substances before they adhere to the tooth surfaces; normal dead cellular (epithelial) material which is continually sloughed off from the surfaces of the oral cavity and microbial degradation products derived from all of the above. Besides the obvious hygienic and health benefits related to simple cleanliness provided by surfactants, there is an important cosmetic and sense-of-well-being benefit provided by surfactant cleansing. Research has shown that the primary source of bad breath is the retention and subsequent degradation of dead cellular material sloughed off continuously by the normal, healthy mouth or dislodged from interproximal surfaces by flossing and not subsequently entrapped and removed by the interproximal device.

Frequency of Cleansing. This is perhaps the most difficult to provide in today's fast-paced work and social environment. Most people recognize that their teeth should be brushed at least 3 times a day and flossed at least once a day. The simple fact is that most of the population brush once a day, some brush morning and evening, but precious few carry toothbrush and dentifrice to use the other three or four times a day for optimal oral hygiene. Consumer research suggests that the population brushes an average of 1.3 times a day. Most surprising, less than 10% of adults floss regularly. Reasons offered for not flossing: difficult to do, painful, does not appear to be working, inconvenient and leaves a bad taste. Overall, floss is not perceived as a "consumer friendly" product.

BRIEF DESCRIPTION OF THE DRAWINGS

FIG. 4a is the tape uncoated. FIGS. 4b and 4c show the tape coated.

KEY DEFINITIONS

For the purposes of the present invention:

"Ultra-high molecular weight polyethylene" is described as having an intrinsic viscosity between about 5 and about 50 dl/g as measured at 135° C. in decalin. These correspond to viscosity-average molecular weights of from between about 1,200,000 and about 6,000,000. These can be obtained by homopolymerizing ethylene or copolymerizing ethylene and an alpha-olefin of 3 or more carbon atoms in the presence of an appropriate catalyst as described in U.S. Pat. No. 5,578,373. Preferably the alpha-olefin has 3 to 12 carbon atoms. See also U.S. Pat. Nos. 4,879,076; 4,998,01; 5,002,714; 5,091,133; 5,106,555; 5,106,558; 5,200,129; 5,598,373; 5,695,708 and 5,723,388. This ultra high molecular weight polyethylene is compressed into films that are stretched and have a tensile strength from between about 0.7 GPa and about 5 GPa.

Figure 1A:
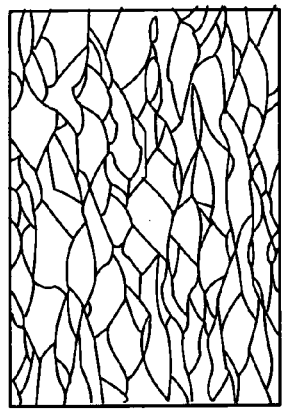
FIGS. 1a through 1f are illustrations of uncoated micromesh tapes suitable for the present invention produced by various rotary fibrillations of stretched, ultra-high molecular weight polyethylene tapes.
Figure 1D:
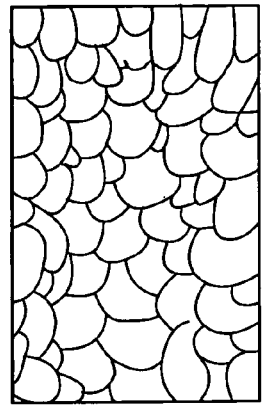
Figure 1B:
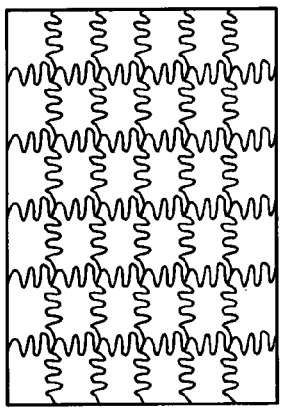
Figure 1E:
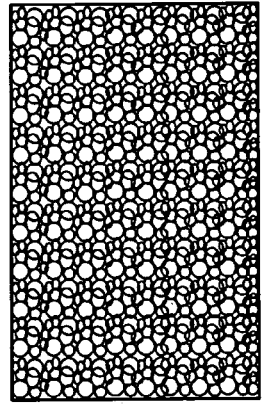
Figure 1C:
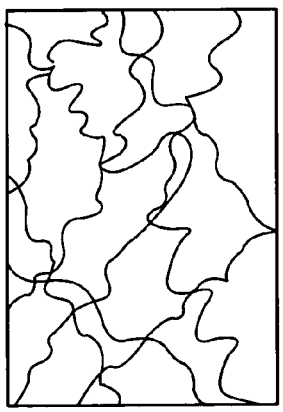
Figure 1F:
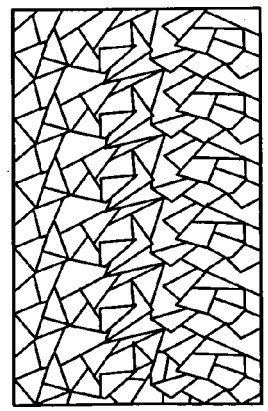
Figure 2A:
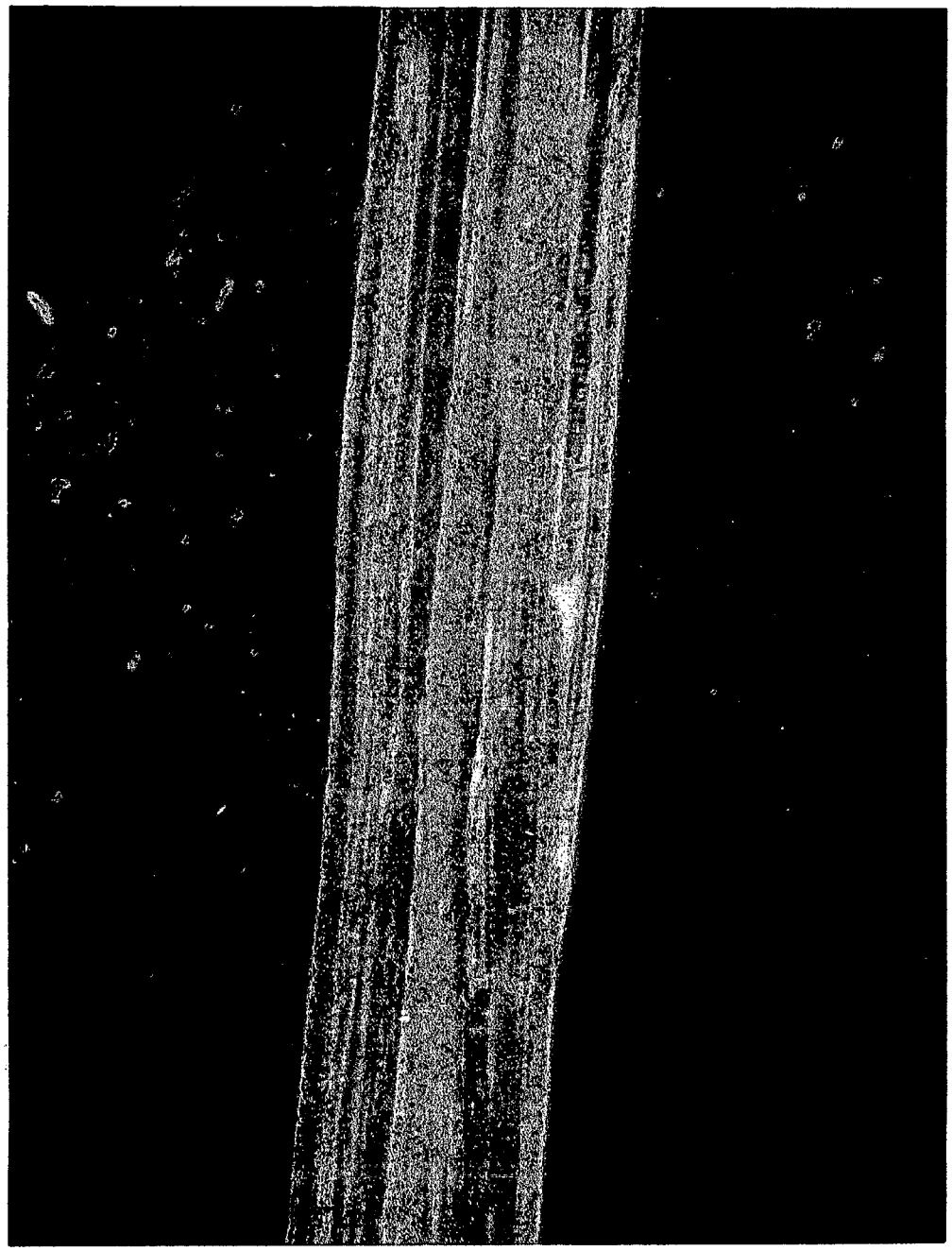
FIGS. 2a through 2c are actual photographs of uncoated micromesh tapes of the present invention.
Figure 2B:
Figure 2C:
Figure 2D:
FIGS. 2d and 2e are photographs of uncoated monofilament dental tape and uncoated multifilament dental floss, respectively.
Figure 2E:
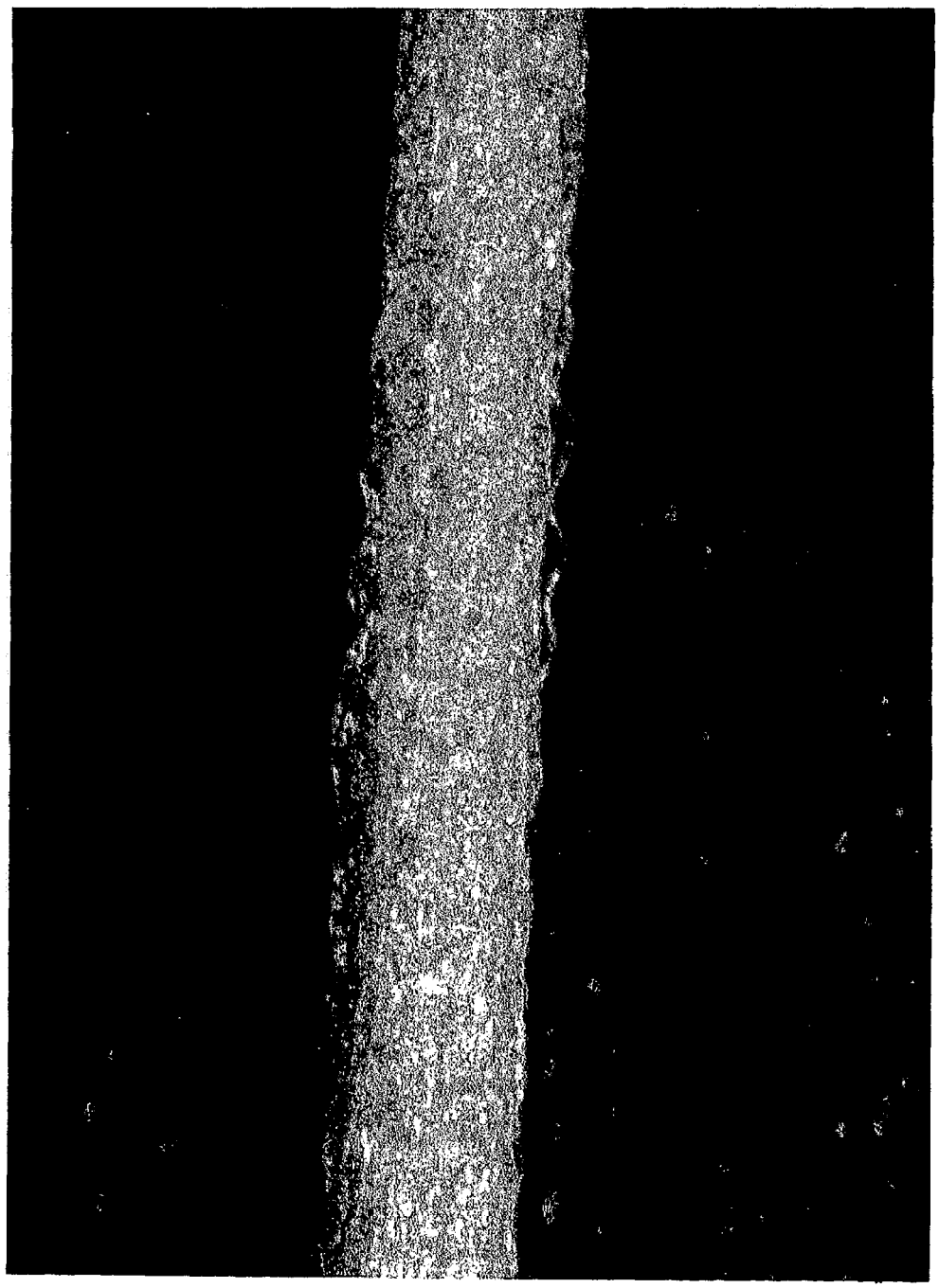
Figure 3A:
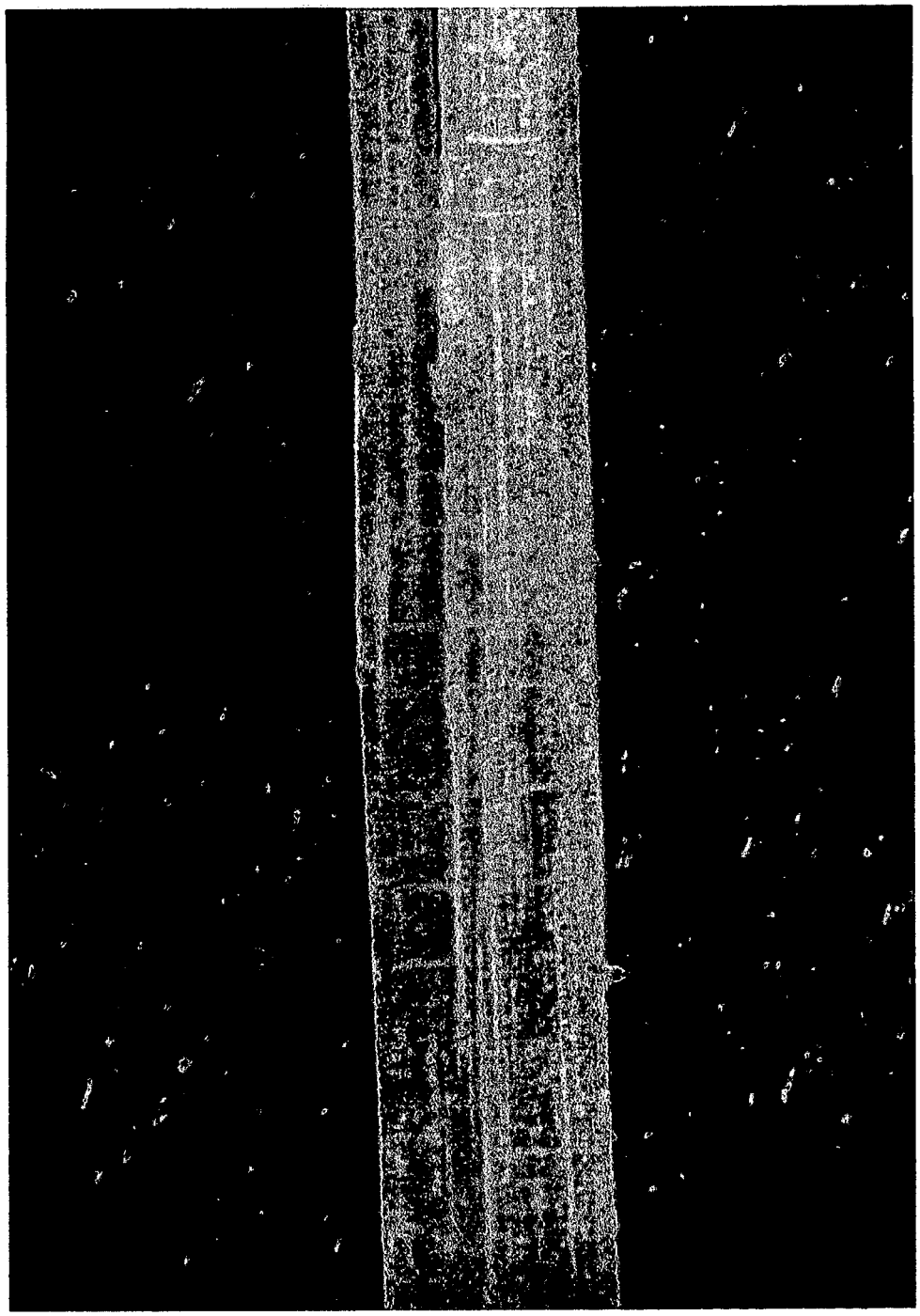
FIGS. 3a and 3b are actual photographs of coated micromesh tapes of the present invention where the tapes are at two different levels of fibrillation.
Figure 3B:
Figure 4A:
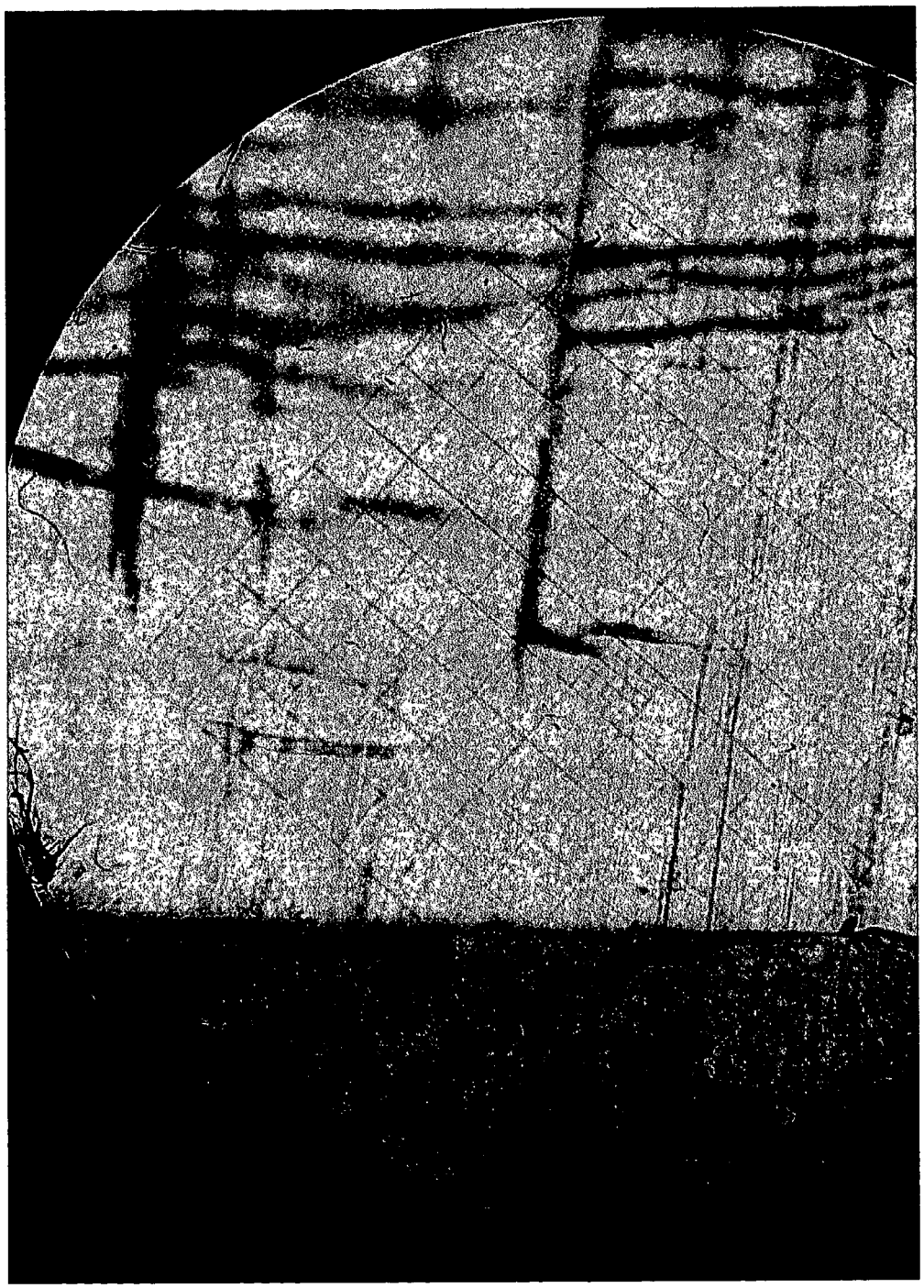
FIGS. 4a through 4c are actual photographs of micromesh tape.
Figure 4B:
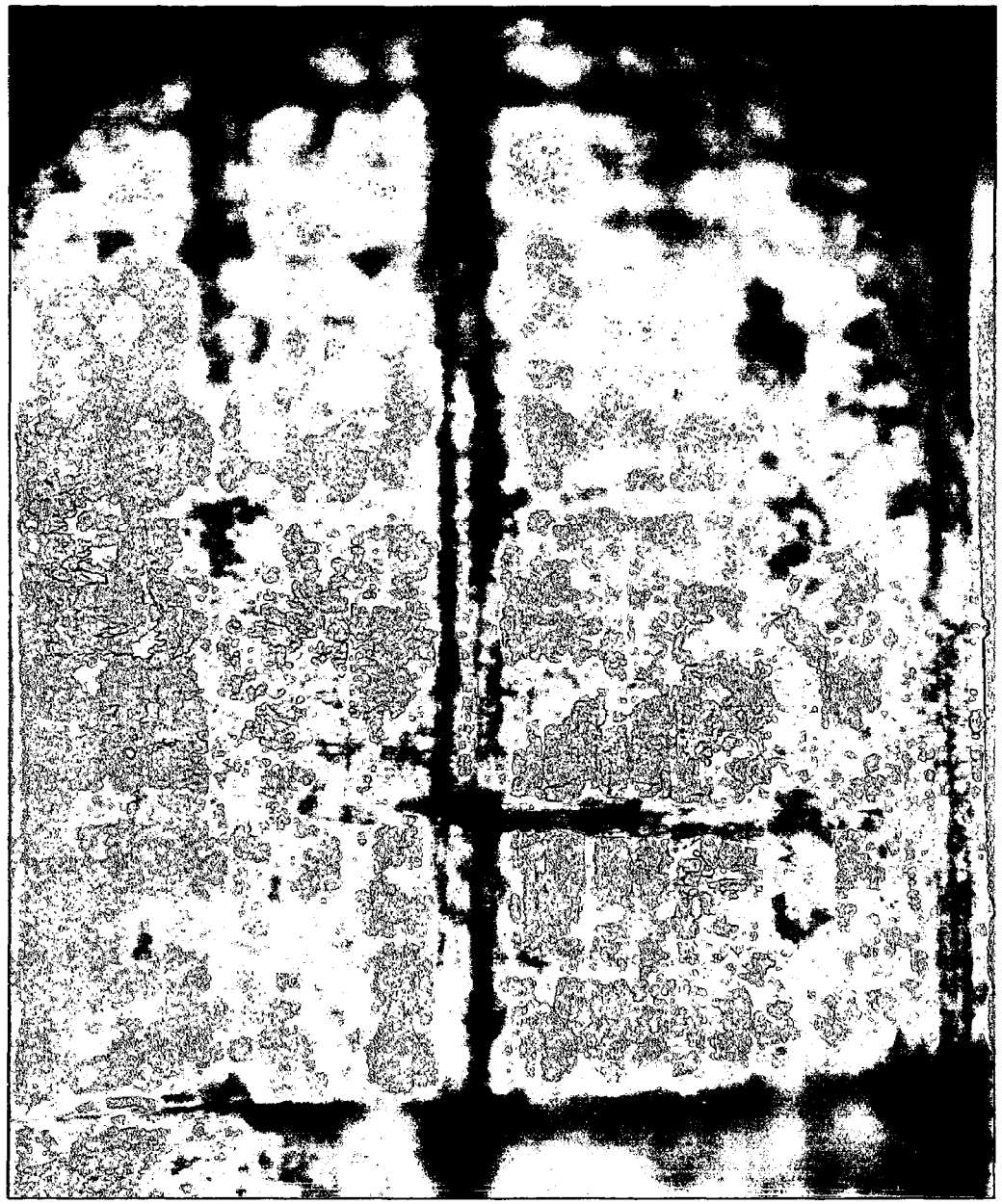
Figure 4C:
Figure 5:
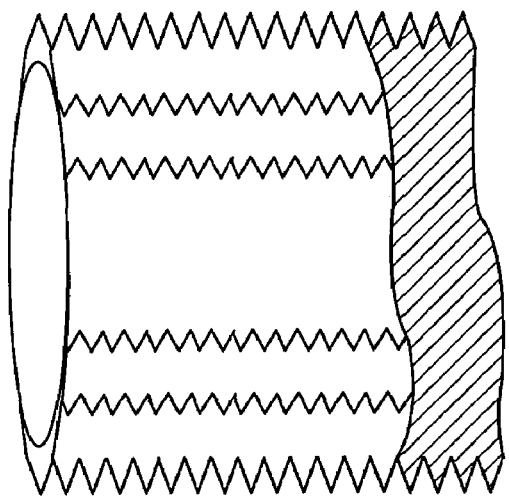
FIG. 5 is an example of a tapping screw-like fibrillator which is hexagonal in shape with 15–35 screw threads per inch.
Figure 6:
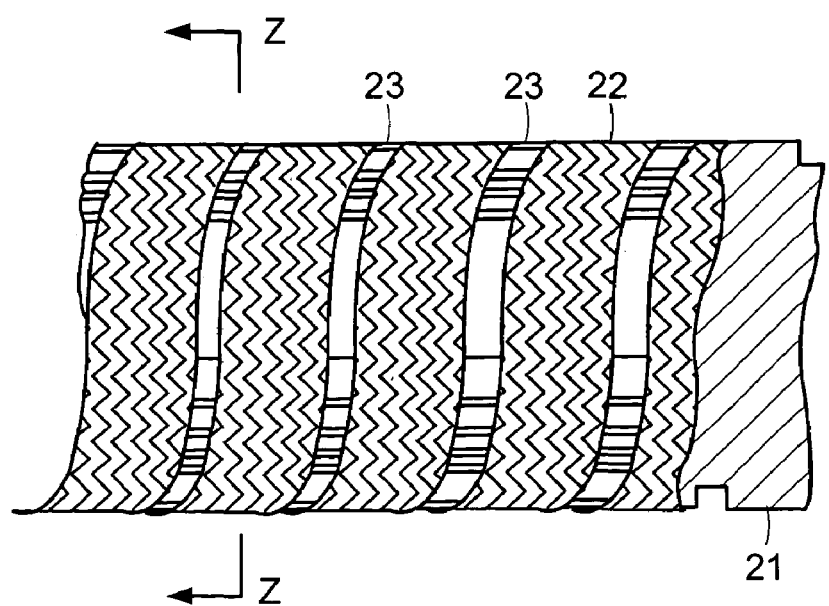
FIG. 6 is an example of a file-like fibrillator having a rough surface similar to the surface of a round file in combination with spiral grooves.

"Fibrillating" is generally defined as a means of converting various high tensile strength, stretched film stocks including tapes to various mesh constructions such as illustrated in FIGS. 1a through 1f and shown in photographs in FIGS. 2 through 4 by subjecting the stretched tapes to contact with various rotary fibrillator means such as shown in FIGS. 5 and 6 as well as described in U.S. Pat. No. 5,578,373; 2,185,789; 3,214,899; 2,954,587; 3,662,930; 3,693,851 and Japanese Publications: 13116/1961 and 16909/1968. During fibrillating, the transfer speed of the stretched polyethylene tape is from between about 1 and about 1000 m/min and the rotational line speed of the fibrillator means in contact with the stretched polyethylene tape is from between about 10 and about 3000 m/min. These fibrillating conditions produce fibrillated tapes suitable for various types of coating including compression loading for use as interproximal devices. See FIGS. 1a through 1f and photographs in FIGS. 2 through 4.

"Fibrillation density" is generally defined as the level of perforations in the interproximal device as determined on the basis of the percent of the device surface that is perforated. Perforations between from about 5% and about 90% of the total tape surface area are suitable for purposes of the present invention. There appears to be a correlation between "fibrillating density" and the capacity of the device to entrap and remove loosened substances from interproximal and subgingival areas, i.e. the "entrapment factor".

"Entrapment factor" is generally defined as the level of biofilm, tartar, debris, etc., which has been dislodged from tooth surfaces during flossing and subsequently entrapped by the micromesh interproximal device after various coating substances have been released from the "spent" interproximal device. The "entrapment factor" is determined by a visual comparison of the spent micromesh interproximal device with a spent commercial monofilament tape used by the same subject at the alternative interproximal site. The micromesh interproximal devices of the present invention generally exhibit entrapment factors from between about 2 and about 10 which indicates a two-fold to ten-fold increase in entrapped debris, biofilm, etc., over the commercial monofilament tape. "Stretched polyethylene tape" is obtained by various drawing methods where the total draw ratio, which is the sum of the draw ratio upon rolling and that upon stretching, is from between about 80 and about 200 fold. See also U.S. Pat. No. 5,578,373.

"Coating" is generally defined as the process of introducing oral care substances onto the micromesh interproximal device by: compression, injection or contact loading means and/or combinations thereof.

"Compression loading" is described as the means for coating various micromesh interproximal devices where the coating substance is generally a high melt viscosity mixture or emulsion which is either doctored onto and/or compressed into the device as it is passed over or between heated rollers with the coating forced into the various interstices of the micromesh tapes being loaded before the excess coating is removed. See FIGS. 11 and 12. All of these methods are collectively described as compression loading, which specifically includes forcing the high melt viscosity mixture or emulsion throughout the micromesh structure. Loaded high melt viscosity coatings from between about 10 and about 120 mg/yd are quite common with the devices of the present invention depending on the particular structure of the tape being "loaded". Compression loading of micromesh tape between heated rollers is particularly effective when Soft Abrasives™ are involved. See the photographs in FIGS. 3 and 4.

Figure 8:
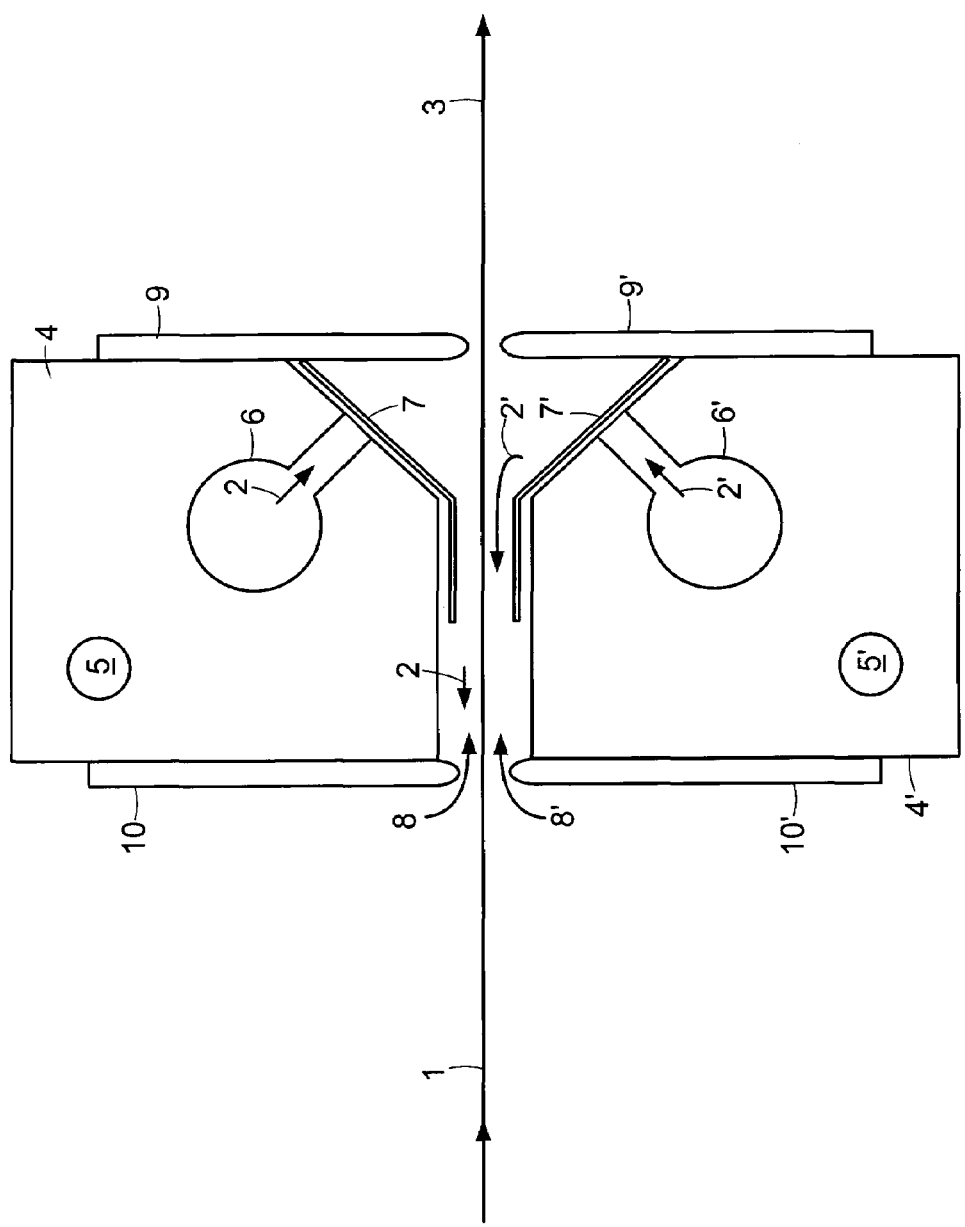
FIGS. 8 through 10 illustrate several injection coating means suitable for coating the micromesh interproximal devices of the present invention.
Figure 9:
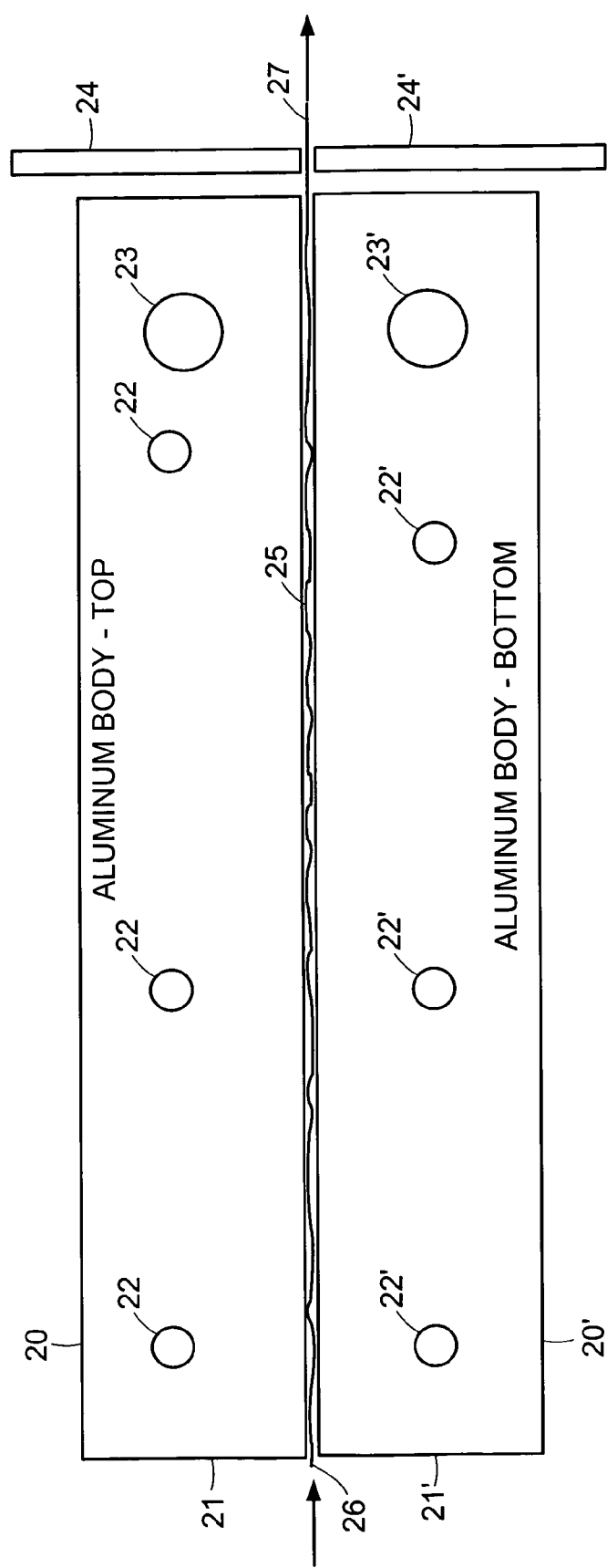
Figure 10:
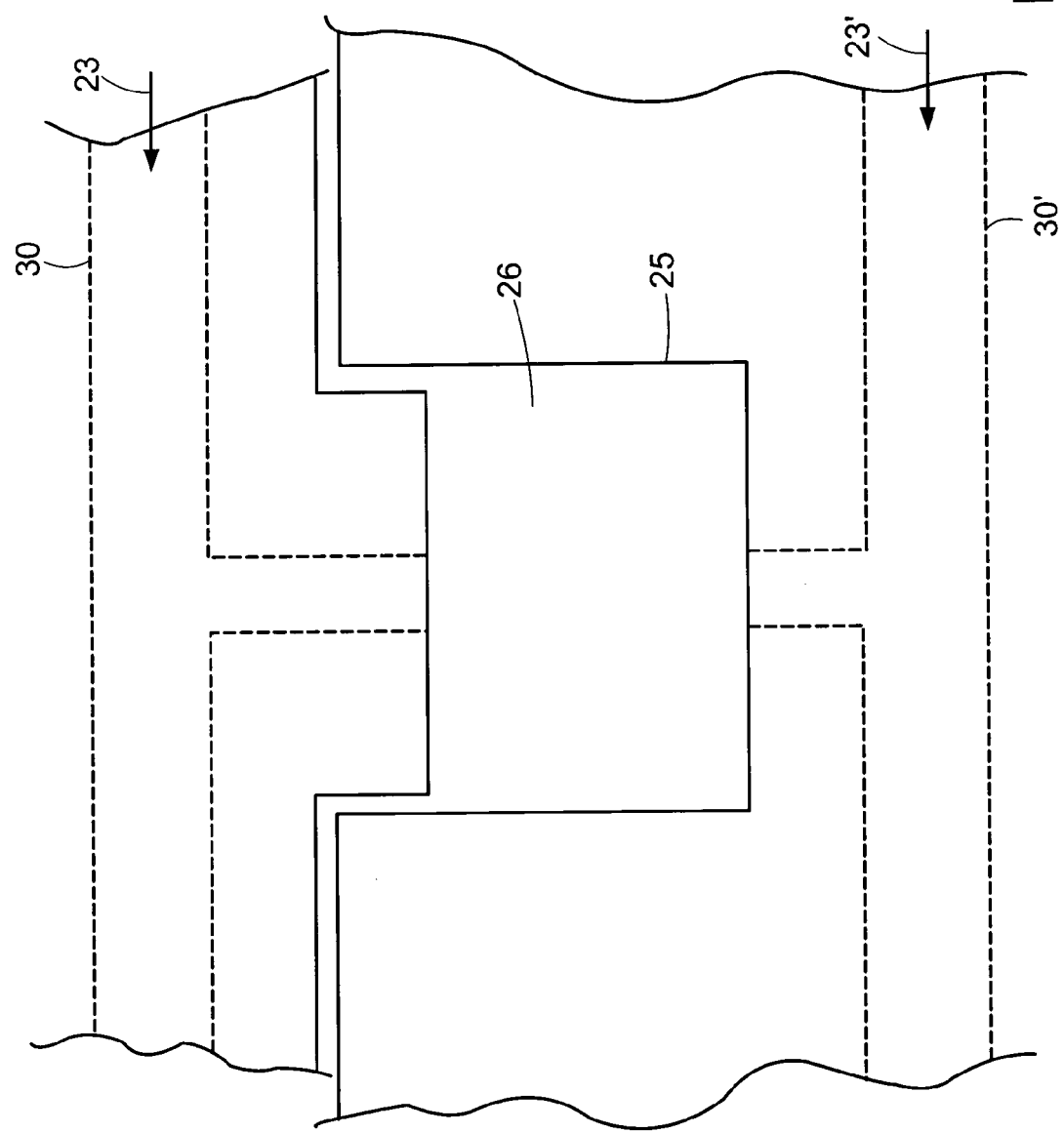

"Injection loading" is described as the means for coating various micromesh interproximal devices where the coating substance is generally a medium melt viscosity mixture or emulsion which is injected onto and/or into the device as it is passed through various injection loading means such as illustrated in FIGS. 8 through 10.

Figure 13:
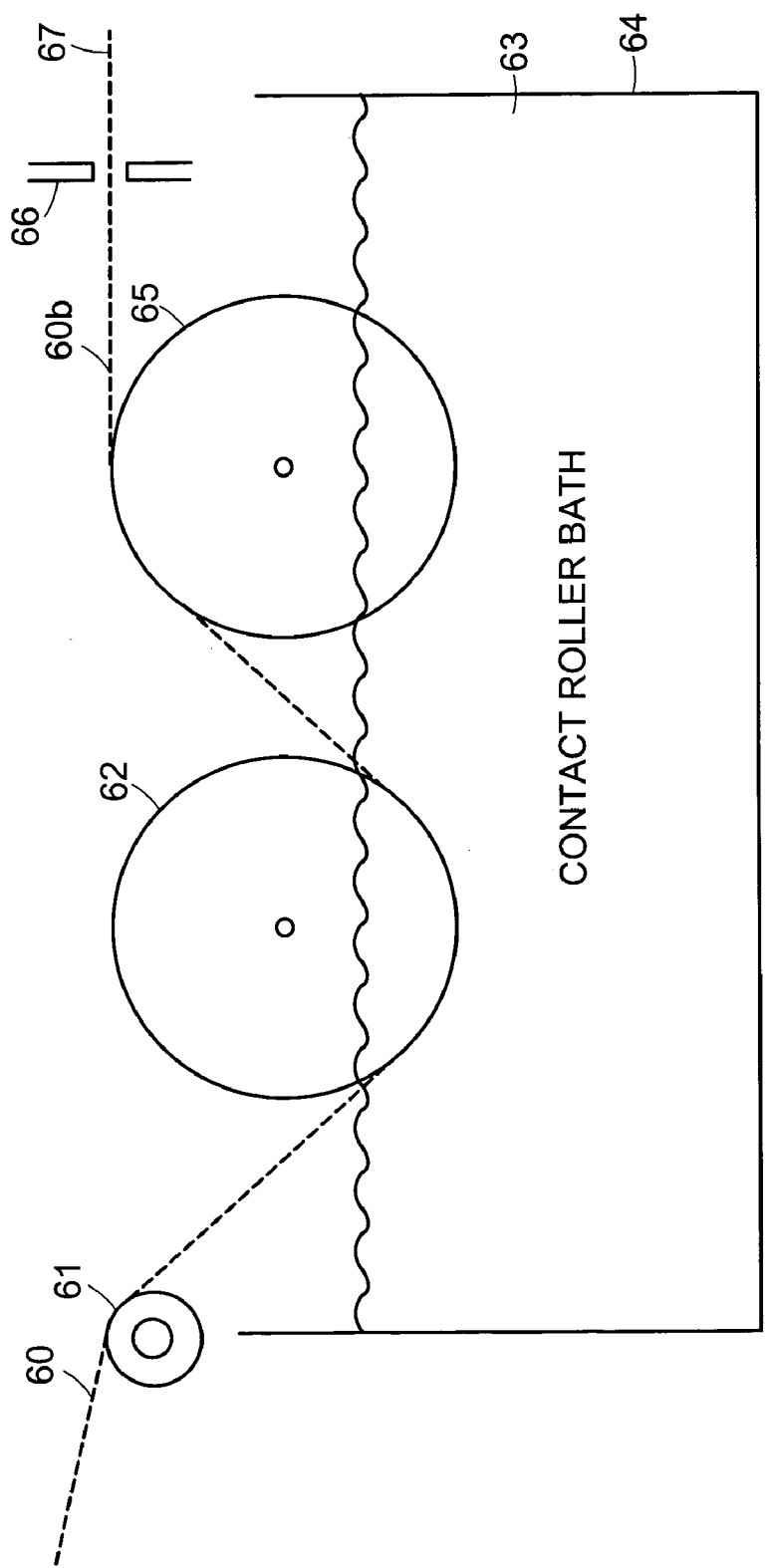
FIG. 13 illustrates contact coating means suitable for coating the micromesh interproximal devices of the present invention.

"Contact loading" is described as the means for coating various micromesh interproximal devices where the coating substance is generally a low melt viscosity mixture or emulsion which is contact loaded onto and/or into the device as it is passed through various contact loading means such as illustrated in FIG. 13.

"Shred resistant" describes the propensity of various interproximal devices to resist shredding, breaking or otherwise becoming discontinuous during flossing. Multifilament devices and particularly texturized multifilament devices tend to be more prone to having individual filaments break and/or shred during flossing than the monofilament tapes. On the other hand, monofilament tapes including PTFE tapes and various extruded monofilament tapes such as Fibaclean Tape™ tend to resist shredding and/or breaking during flossing due to their single monofilament construction combined with the low surface energy property of the tape. That the micromesh devices of the present invention exhibit ultra shred resistant properties is totally surprising and unexpected considering the random: mesh, web or honeycomb construction of these devices as illustrated in FIGS. 1a through 1f and the photographs shown in FIGS. 2 through 4. The ultra high molecular weight and exceptional tensile strength of the fibrillated micromesh polyethylene tape, combined with the "lubricants" in the compression loaded saliva-soluble, crystal-free coatings of the devices is believed to be primarily responsible for the exceptional shred resistance of the devices of the present invention.

"Micromesh" is described as a random: net, web or honeycomb-type, integrated structure as distinguished from the more orderly monofilament and multifilament or woven structures used heretofore for interproximal devices. These micromesh structures are produced at low cost by integrating a rotating fibrillator device into a flat, stretched film or tape producing operation such as described in U.S. Pat. No. 5,578,373. A wide range of fibrillators are available to produce an almost endless array of micromesh structures including those illustrated in FIGS. 1a through 1f and further shown in Photographs, FIGS. 2 through 4. All of these are suitable for use as interproximal devices of the present invention. The fibrillating density of these micromesh interproximal devices is defined above.

"Coatings" are generally described as various oral care substances suitable for compression loading, injection loading and/or contact loading which include high, medium and low melt viscosity mixtures and emulsions as described in Tables 1 through 6.

Figure 11:
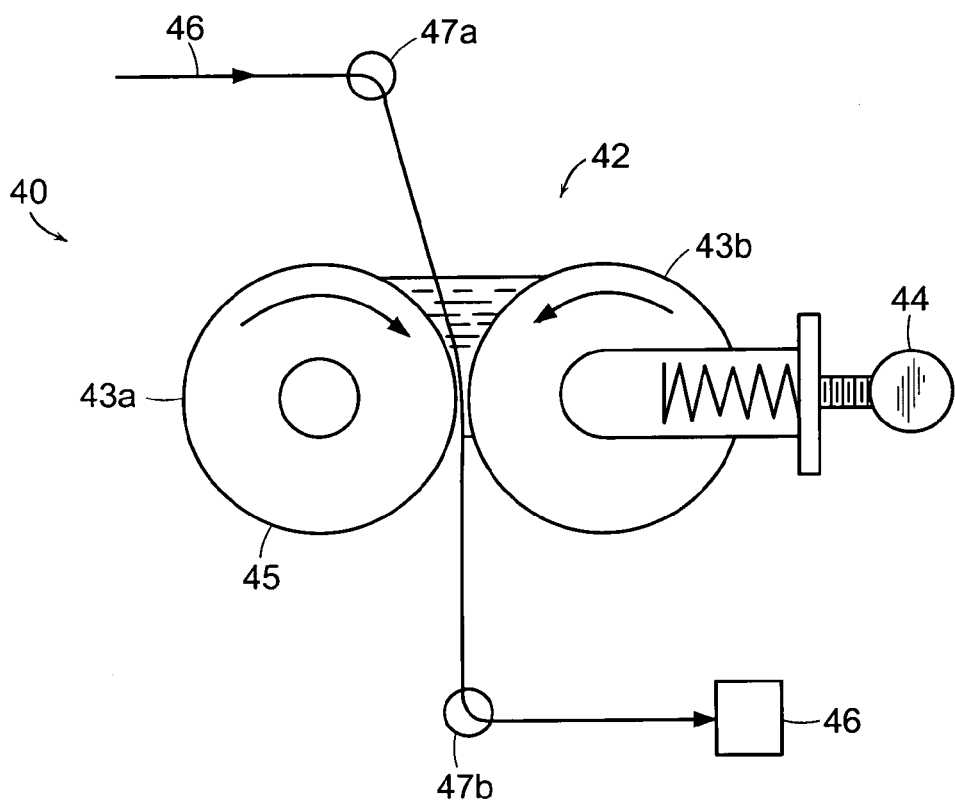
FIGS. 11 through 12 illustrate compression coating means suitable for coating the micromesh interproximal devices of the present invention.
Figure 12:
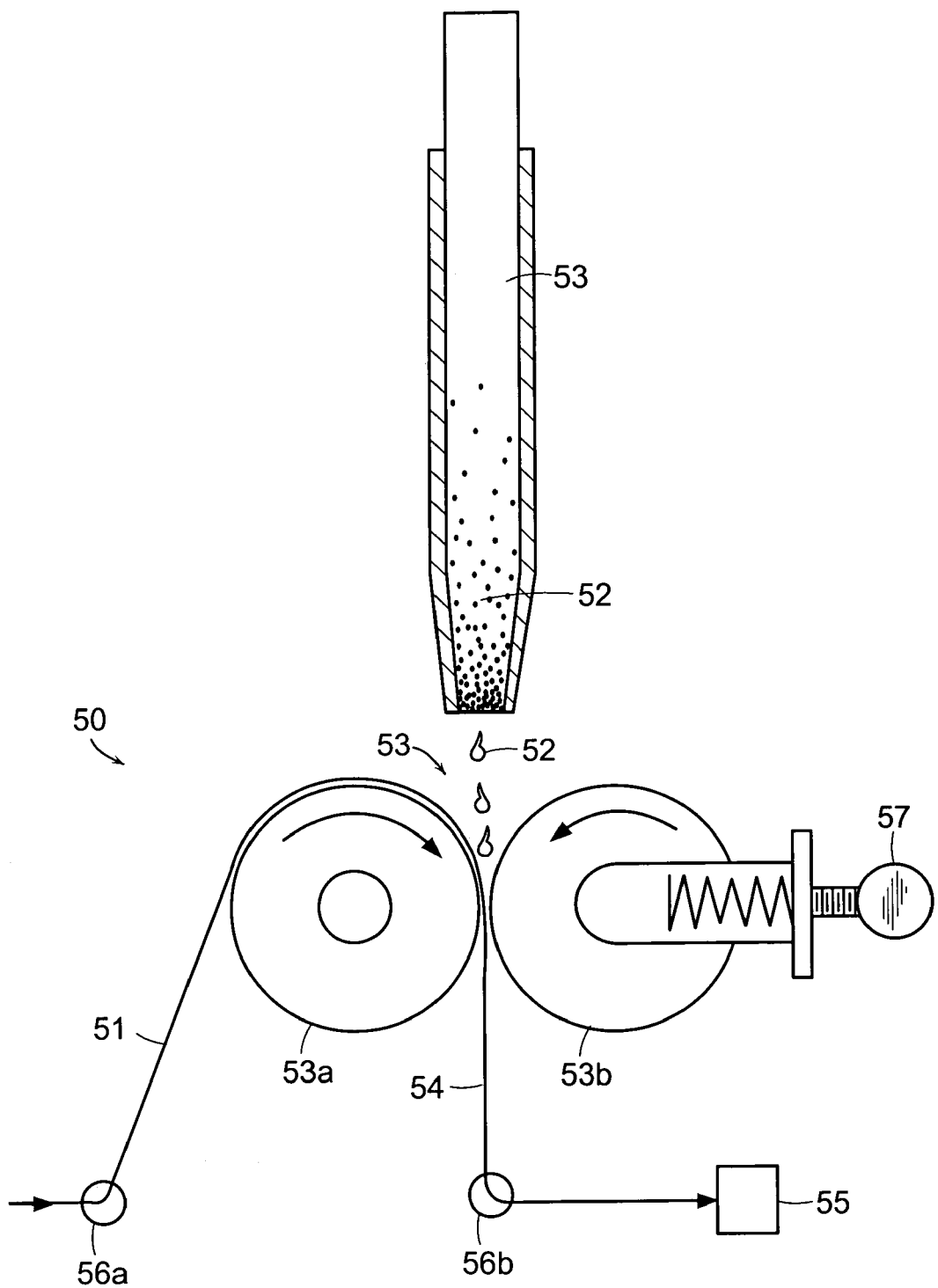

"High melt viscosity mixtures and emulsions" are generally described as those oral care substances generally loaded onto and/or into the micromesh interproximal devices of the present invention using compression loading means such as illustrated in FIGS. 11 and 12 and further described in detail in Tables 1 through 4.

"Medium melt viscosity mixtures and emulsions" are generally described as those oral care substances generally loaded onto and/or into the micromesh interproximal devices of the present invention using injection loading means such as illustrated in FIGS. 8 through 10 and further described in detail in Table 5.

"Low melt viscosity mixtures and emulsions" are generally described as those oral care substances generally loaded onto and/or into the micromesh interproximal devices of the present invention using contact loading means such as illustrated in FIG. 13 and further described in detail in Table 6.

"MICRODENT®" and "ULTRAMULSION®" are emulsions of polydimethylsiloxane at various molecular weights in various poloxamer surfactants as described and claimed in U.S. Pat. Nos. 4,911,927; 4,950,479; 5,032,387; 5,098,711; 5,165,913; 5,538,667; 5,645,841; 5,561,959 and 5,665,374. These mouth conditioners are preferably included in the various crystal-free coatings of the present invention.

Figure 7:
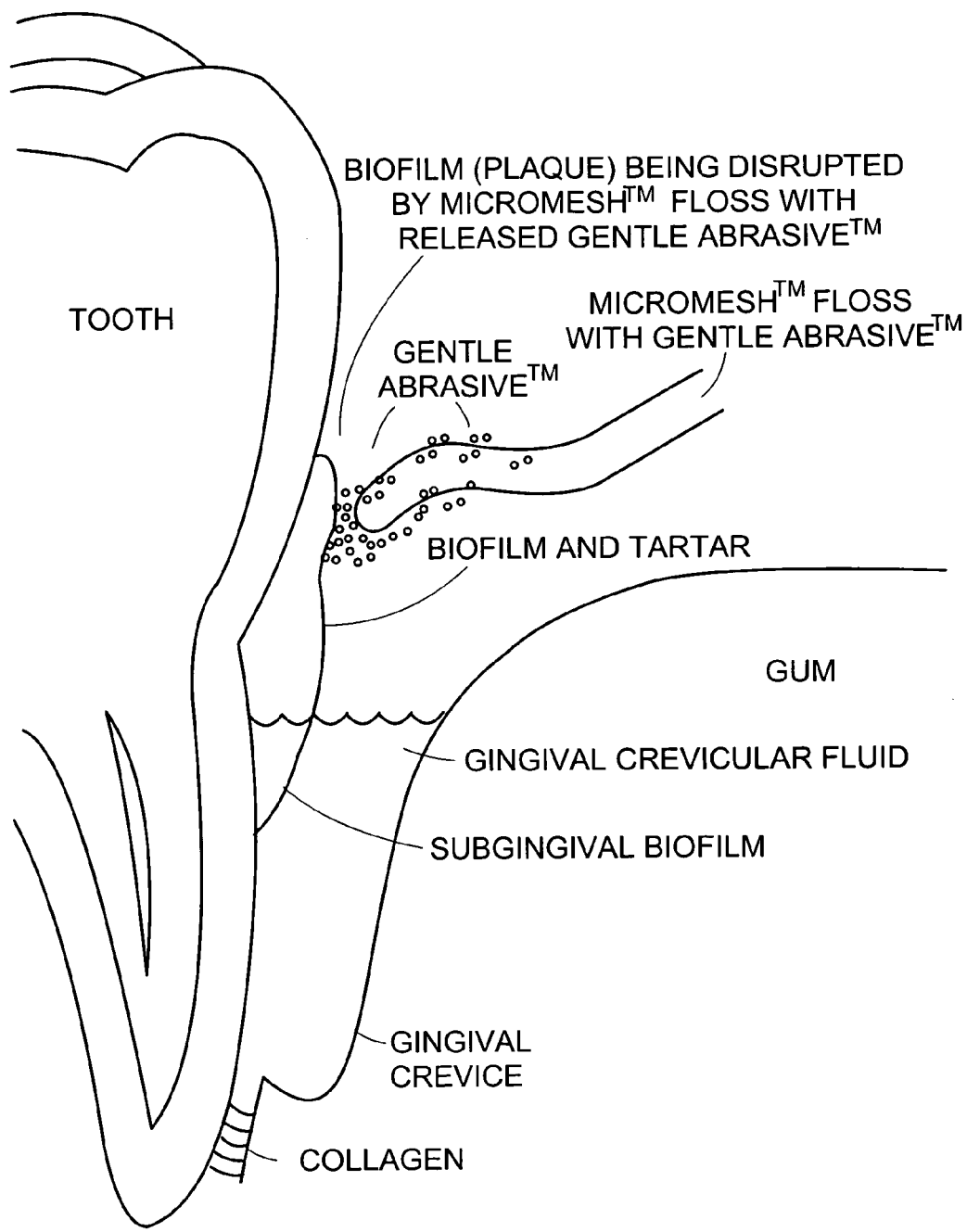
FIG. 7 is a schematic diagram of coated micromesh interproximal device of the present invention scrubbing Soft Abrasives™, released from the device coating during flossing, across a tooth surfaces to remove biofilm and tartar deposits.

"Saliva-soluble, crystal-free coatings" include those compression loaded, high melt viscosity mixture and emulsion coatings that release from the micromesh devices of the present invention during flossing when exposed to saliva in the oral cavity. These coatings can include Soft Abrasives™ that are dispersed and not solubilized in said coatings. These Soft Abrasives™ remain insoluble when delivered between teeth and below the gum line during flossing. Additionally, saliva-soluble coatings preferably contain surfactants, mouth conditioners, chemotherapeutic ingredients and flavors that are released from the micromesh devices into the oral cavity during flossing. See photographs in FIGS. 3 and 4 and the schematic illustration set out in FIG. 7.

"Crystal-free" is defined as a smooth surface as distinguished from rough surface typical of crystalline coatings when observed through a 30× stereo zoom microscope. Examples of suitable coating formulations are detailed in Examples 9 through 26 in Table 3 below.

"Soft Abrasives™" include saliva-soluble and saliva-insoluble abrasive substances suitable for cooperating with the micromesh structure of the devices of the present invention to scrub biofilm, tartar and stained pellicle from tooth surfaces. Soft Abrasives™ include tetra sodium pyrophosphate, calcium carbonate, dicalcium phosphate, silica, glass beads, polyethylene and polypropylene particles, pumice, titanium oxide, alumina, quartz, aluminum silicate, etc., at various particle sizes suitable for use in oral care.

"Whitening agents" for extrinsic stains include: those which function by means of oxidation such as carbamide peroxide and hypochlorites; those which function by interfering with calcium complex deposits such as tetrasodium phosphate or sodium hexametaphosphate and various chelating agents and the "Soft Abrasives™" described above for stained pellicle removal.

"Cleaners" include essentially all surfactants suitable for use in the oral cavity and suitable for coating the micromesh structure of the interproximal devices of the present invention.

"Chemotherapeutic ingredients" include those substances suitable for addition to the coatings of the present invention that impart therapeutic effects to the oral cavity including antimicrobials; anti-tartar and anti-plaque substances; remineralizing, desensitizing, NSAID and antibiotic ingredients; and the like. Specific chemotherapeutic ingredients suitable for the present invention include: stannous fluoride, potassium nitrate, cetylpyridinium chloride (CPC), triclosan, metronidazole, chlorhexidine, aspirin and doxycycline.

"Substantially flake-free" refers to the propensity of the coatings of the present invention to resist flaking off micromesh dental flosses during flexure. Flaking resistance is based on the reduction by weight of the crystal-free coating after flexing, under suitably controlled and reproducible conditions, where an 18-inch piece of the coated micromesh floss is flexed for 30 seconds.

"Release value" is measured after 18-inches of the micromesh floss is thoroughly flossed for 60 seconds. The percent of the coating removed from the micromesh floss during flossing establishes the release value.

"Formula modifiers" are those ingredients which are otherwise inactive as cleaners, abrasives or chemotherapeutic agents. Formula Modifiers allow convenient control of the desired melt viscosity of the coating, help provide the desired release rate in the mouth, help provide for desired dispersability properties in the manufacturing process and improve mouthfeel for consumer acceptance.

SUMMARY OF THE INVENTION

The present invention relates to innovative interproximal devices that are distinct from and superior over multifilament dental flosses, as well as monofilament dental tapes. These superior performing interproximal devices are neither multifilament nor monofilament in structure. Rather, they are characterized by a unique micromesh honeycomb or web-type structure, hereinafter described as a micromesh structure. These micromesh devices are not produced from a bundle of fibers like multifilament dental flosses nor are they produced by slitting shred-resistant films used to manufacture PTFE tape or by extrusion used to manufacture elastomeric monofilament tapes and/or the extrusion and slitting processes used to make typical high density polypropylene or polyethylene tapes. Rather, these ultra shred-resistant micromesh devices are produced by fibrillating and slitting high-tensile strength, ultra-high molecular weight, stretched, polyethylene films. This fibrillation of stretched polyethylene films produces various micromesh structures such as illustrated in FIG. 1 of the drawings and further depicted in the photographs in FIGS. 2 through 4. The photographs in FIG. 2 compare typical uncoated multifilament and monofilament devices with uncoated micromesh tapes of the present invention. The Photographs in FIG. 3 show coated micromesh interproximal devices at two different levels of fibrillation. The photographs in FIG. 4 illustrate a micromesh tape coated and uncoated.

The micromesh structure is an ideal substrate for loading with various coatings using compression, injection and contact loading processes as described in detail below and illustrated in FIGS. 8 through 13. These "loaded" micromesh devices exhibit minimum flaking yet readily release their coatings during flossing.

Saliva-soluble, substantially crystal-free coatings such as described in detail below are particularly preferred when compression loaded onto these micromesh tapes using the compression loading technology described below.

More specifically, the present invention relates to an ultra-shred resistant, high-molecular weight polyethylene micromesh interproximal device produced by:

1. fibrillating and slitting stretched polyethylene film having a tensile strength between about 0.7 GPa and about 5 GPa, wherein the polyethylene has an intrinsic viscosity of from between about 5 and about 50 dl/g, wherein the fibrillation uses various rotary fibrillator devices such as those shown in FIGS. 5 and 6 to produce a micromesh structure, such as shown in FIGS. 1a through 1f and the photographs shown in FIGS. 2 through 4, and 2. compression, injection or contact loading said micromesh structure with one of the various coatings described in Tables 1 through 6 below. Preferably this coating comprises cleaners, chemotherapeutic substances, mouth conditioners and Soft Abrasives™ at from between about 10 and about 120 mg/yd.

Referring to FIGS. 8 through 13:

In FIG. 8, which is a side view of an injector coating means, 4 and 4¹, suitable for coating the micromesh interproximal device, 1, with medium melt viscosity coating mixtures or emulsions, 2 and 2¹, to produce injection coated interproximal device, 3.

Interproximal device, aluminum injector coating means, 4 and 4¹, are provided with rod-type heating elements means, 5 and 5¹, to heat coatings, 2 and 2¹.

Coatings, 2 and 2¹, are pumped under pressure through manifold means, 6 and 6¹, flowing between laminar flow means, 7 and 7¹, filling the chamber, 8 and 8¹, defined by metering plate means, 9 and 9¹, and flow control plate means, 10 and 10¹.

Coatings, 2 and 2¹, are pumped through chambers, 8 and 8¹, counter to the movement of interproximal device, 1, to optimize shear. Adjustment of the gap between metering plate means, 9 and 9¹, controls the level of coatings, 2 and 2¹, on device, 1, that emerges from coating means, 4 and 4¹, as injection coated interproximal device, 3. Injection loader means, 4 and 4¹, can accommodate coating up to 32 interproximal devices simultaneously.

In FIG. 9 which is a cross-sectional side view of a single line injection coating means, 20 and 20¹, comprises aluminum body means, 21 and 21¹, provided with heating means, 22 and 22¹.

Coating liquids, 23 and 23¹, are pressure fed to manifolds, 24 and 24¹, and then forced into channel means, 25, counter to the movement of micromesh device, 26, to produce the injection coated micromesh device, 27. Metering plate means, 25 and 25¹, allow for adjusting plate means, 28 and 28¹, to control injection coating levels.

The use of channel means, 25, keeps micromesh device, 26, separated physically so that any breakage is contained and does not affect neighboring device lines.

FIG. 10 is a detailed cross-sectional view of channel arrangement means, 25, shown in FIG. 9. Injection coating supply manifolds, 30 and 30¹, deliver coating liquids, 23 and 23¹, to channel means, 25, under pressure in a direction counter to the movement of micromesh device, 26.

FIGS. 11 and 12 are cross-sectional views of schematic compression loading means, 40 and 50, suitable for coating micromesh interproximal devices, 41 and 51 respectively, with high melt viscosity mixtures or emulsions, 42 and 52 respectively.

Referring to FIG. 11, the high melt viscosity emulsion, 42, to be loaded into micromesh tape, 41, is maintained between heated nip roller means, 43a and 43b. Nip roller, 43b, is provided with adjustable tension means, 44, which controls the compression on micromesh tape, 41, while avoiding damage to tape during loading. These nip rollers provide some of the pulling force and impart sufficient tension to assist driving coating, 42, onto and into micromesh tape during the compressing/loading step. Loaded micromesh tape, 45, is wound on take up means, 46.

The compression force obtained with the nip rollers is sufficient to load substantial quantities of coating, 42, while passing through this system at speeds between 2 and 20 ft/sec. Six to 10 ft. sec is a convenient speed. Various guides, 47a and 47b, are positioned to assist and guide floss, 21, through the system.

Generally, coatings, 42, are maintained in a molten state at temperatures ranging from between about 180° F. and about 250° F. By controlling the viscosity of coating, 42, the flow of these coatings into nip rollers, 43a and 43b, can be maintained.

Preparations suitable for loading include those set out in Tables 1 through 4 below.

Referring to FIG. 12, high melt viscosity emulsion coating, 52, is heated in tip applicator, 53, which maintains coating, 52, in a liquid state. Coating, 52, is metered onto compressing means, 53, comprising heated nip roller means, 53a and 53b.

Untreated micromesh tape, 51, passes over nip rollers, 53a, and is compressed by nip roller, 53b, while coating, 52, is forced onto and into the micromesh structure of tape, 51. Treated tape, 54, is then wound onto take up means, 55. Various floss guides, 56a and 56b, are positioned to assist the travel of tape, 51, and guide untreated tape 51, and treated tape, 57, which controls the compression force applied to tape, 51, while avoiding physical damage to the tape during loading of coating, 52.

Coating, 52, is maintained as a melt by maintaining the temperature in tip applicator, 53, at approximately 210° F. Rate of application of coating, 52, is approximately 1.85 g/min. The quantity of coating loaded into micromesh tape, 51, is controlled by:

1. the flow rate of coating, 52, from applicator;
2. the speed of nip rollers, 53a and 53a;
3. nip roller, 52b, tension, as determined by the adjustment of tension means, 57;
4. the preparation and viscosity of coating, 52; and
5. the fibrillation density of micromesh tape, 51.

Referring to FIG. 13:

Micromesh floss, 60, passes over godet, 61, and under contact roller means, 62, which is partially immersed in low melt viscosity emulsion coating, 63, contained in contact roller coated teeth means, 64, coating the upper surface, 60a, of floss, 60, with coating, 63; partially coating floss, 60, then passes over contact roller means, 65, which is also partially immersed in low melt viscosity emulsion coating, 63, thereby coating the under surface, 60b, of floss, 60, with coating, 63. The coating levels of 60a and 60b on micromesh floss, 60, are controlled by passing coated micromesh floss, 60, through metering gap means, 66. Coated and metered floss, 67, is then processed through a traditional drying means or onto a traditional winding means, neither of which are shown.

DETAILED DESCRIPTION OF THE INVENTION

The interproximal devices of the present invention can contain a broad range of coating substances which are best loaded onto and/or into the micromesh structure by one of three loading means. Specifically:

1. the high melt viscosity mixtures and emulsions are loaded onto and/or into the micromesh by compression means. These are detailed in the examples set out in Tables 1 through 4 below;
2. the medium melt viscosity mixtures and emulsions are loaded onto and/or into the micromesh by injection loading means. These are detailed in the examples set out in Table 5 below, and
3. the low melt viscosity mixtures and emulsions are loaded onto and/or into the micromesh by contact loading means. These are detailed in the examples set out in Table 6 below.

The improved interproximal devices of the present invention contain coatings that: (a) comprise from 10 to 120% by weight of the micromesh substrate, (b) are preferably saliva soluble and (c) in a preferred embodiment are crystal free, and accordingly, exhibit a minimum of flaking. Some of these coatings are released in total into the oral cavity during flossing. In a preferred embodiment, these coatings contain ingredients such as: (a) Soft Abrasives™ that work with the micromesh structure to help physically remove biofilms (plaque) from interproximal and subgingival surfaces, (b) chemotherapeutic ingredients affecting oral health and subsequent systemic diseases caused or exacerbated by poor oral health, (c) cleaners that introduce detersive effects into the areas flossed, and (d) mouth conditioners. These coatings are particularly adapted to loading into and/or onto the micromesh tapes using the compression, injection or contact loading means described above to produce the innovative interproximal devices of the present invention.

It has been discovered that the substantivity of certain high melt viscosity mixture and emulsion coatings loaded onto micromesh tapes can be enhanced such that during flexure of the coated micromesh floss, these enhanced coatings remain substantive to said floss and resist cracking, fracturing and flaking off. Specifically, it has been observed that most coated flexible surfaces, especially those formulated to be saliva-soluble and to carry effective quantities of abrasives, cleaners, surfactants, and chemotherapeutic agents; fracture along crystal faces during flexure of the floss, thereafter prematurely releasing the ingredients from the flexible surface by cracking, chipping, flaking and/or falling off, etc. In response to these observations, it has been unexpectedly found that the addition of certain substances to various high melt viscosity mixture and emulsion coatings at relatively modest levels reduces crystal formation while simultaneously enhancing the coating's substantivity to these micromesh flosses when subjected to flexure, which properties thereby impart outstanding flake resistance and release values to said micromesh interproximal devices of the invention.

Those coating additives that reduce, control and/or eliminate crystal formation and enhance the substantivity of the loaded coating to flexible, micromesh surfaces when added to these coatings at modest levels include certain aliphatic, long chain, fatty alcohols having from between about 10 and 30 carbon atoms and/or various liquid surfactants such as polyethylene glycol sorbitan dialiphatic esters.

Suitable aliphatic, long chain, fatty alcohols for the crystal-free coatings of the present invention can be represented by the structural formula ROH, wherein R represents a long chain alkyl group having from 20 to 30 carbon atoms. Specific examples include:

| 1-decanol | 1-heptadecanol | 1-pentacosanol |
|---|---|---|
| 1-undecanol | 1-octadecanol | 1-hexacosanol |
| 1-dodecanol | 1-nonadecanol | 1-heptacosanol |
| 1-tetradecanol | 1-eicosanol | 1-octacosanol |
| 1-pentadecanol | 1-heneicosanol | 1-nonacosanol |
| 1-hexadecanol | 1-tricosanol | 1-triacosanol |
| 1-tetracosanol, and mixtures thereof. | | |

Naturally occurring mixtures with substantial quantities of these fatty alcohols, or isomers thereof; including those chemically derived from natural sources also constitute suitable sources of aliphatic, long chain fatty alcohols for the purpose of this invention.

The long chain fatty alcohols can be purchased commercially from Stepan, Procter & Gamble and Aldrich Chemical Co. and a variety of companies processing vegetable and animal derived fatty alcohols.

Suitable liquid surfactants for the saliva-soluble, crystal-free coatings of the present invention include polyoxyethylene glycol sorbitan mono- and di-aliphatic esters represented by the general formula:

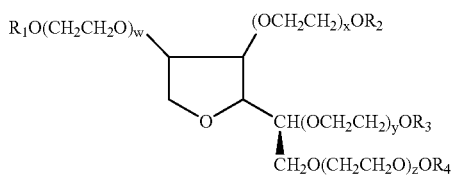

wherein $R_1$, $R_2$, $R_3$, $R_4$ are H or aliphatic acyl groups having from between about 10 and 30 carbon atoms, and the sum of w, x, y, and z is from between about 20 and about 80. These liquid surfactants are available under the trade names Emsorb®, Span®, Tween® from Cognis, N.A. and ICI. Specific examples of these include:

PEG 20 sorbitan monooleate (Tween® 80, ICI); PEG 40 sorbitan monostearate (SPAN 60 ICI) and PEG 40 sorbitan diisostearate (Emsorb 2726, Cognis N.A.).

Surprisingly, interproximal devices of the present invention feature ultra shred-resistance combined with superior gentleness. The loaded coating released during flossing can deliver cleaners, mouth conditioners, chemotherapeutic ingredients, etc., along with Soft Abrasives™ between teeth and below the gum line. These substances also collectively impart lubricity to the interproximal devices. This micromesh structure combines with the Soft Abrasives™ released during flossing to gently scrub biofilm, tartar and stained pellicle from tooth surfaces between teeth and below the gum line.

Figure 7A:
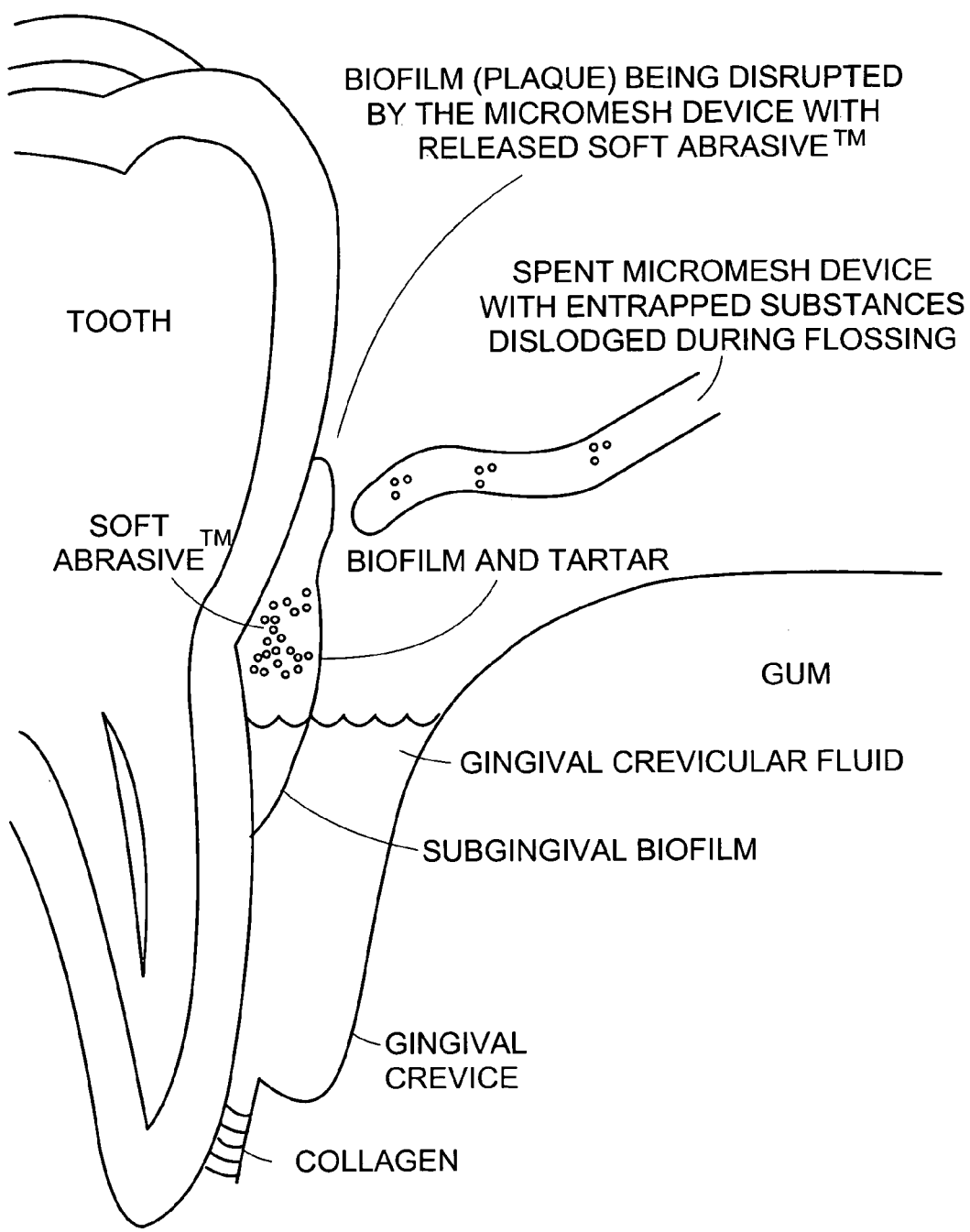
FIG. 7A is a schematic diagram of a "spent" micromesh interproximal device of the present invention, after flossing, showing the dislodged substances entrapped in the device and removed from interproximal and subgingival areas.

Once the micromesh interproximal device has released the coating during flossing, it tends to simultaneously entrap loosened biofilm, tartar and stain residue, along with other debris and to then remove these entrapped substances from between teeth. See FIG. 7a. The capacity to entrap and remove loosened biofilm, etc., from between teeth is a most critical function of effective interproximal devices according to Bass [*Dental Items of Interest*, 70, 921–34, (1948)].

This feature of the interproximal devices of the present invention is described as the entrapment factor. As noted above, the "entrapment factor" has been generally compromised by monofilament dental tapes and by most multifilament waxed flosses available commercially today. Surprisingly, compression and injection loading of the micromesh tape with high and medium melt viscosity mixtures and emulsions containing Soft Abrasives™ tends to accentuate the fibrillations in the tape, which tends to make these fibrillations more effective in entrapping loosened substances and in removing them from between teeth once the coatings are released.

The entrapped biofilm, tartar, stain residue and debris removed from between teeth by these micromesh devices, i.e. the entrapment factor is readily visually indicated on the "spent" floss, and serves to help motivate compliance. See FIG. 7a.

The micromesh structure, in combination with the Soft Abrasives™ loaded into and on the micromesh interproximal device which is later released during flossing, creates a perceptible impression that the device is working to remove biofilm, tartar, stained pellicle, debris, etc., as the device is being worked (usually with a sawing-action) between teeth. This "it's working" perception is a critical "compliance" advantage over most multifilament and monofilament dental devices available commercially.

The preferred saliva-soluble, substantially crystal-free, high and medium melt viscosity mixture and emulsion coatings of the invention can contain various cleaners, Soft Abrasives™, chemotherapeutic ingredients, as well as flavors, mouth conditioners, etc. These latter substances tend to leave a lasting coating on surfaces in the oral cavity that imparts a refreshing, just-brushed feeling that also encourages and motivates regular flossing, particularly after meals and snacks while away-from-home. Particularly preferred mouth conditioners include various MICRODENT® and ULTRAMULSION® substances such as described in U.S. Pat. Nos. 4,911,927; 4,950,479; 5,032,387; 5,098,711; 5,165,913; 5,538,667; 5,645,841; 5,561,959 and 5,665,374.

The mechanical action of the micromesh structure in combination with Soft Abrasives™ released in the various coatings during flossing is further supplemented by the various cleaners including surfactants also released in these coatings during flossing. These released cleaners are readily soluble in the saliva and interproximal fluids and produce a detersive effect in the interproximal and subgingival regions. This detersive effect is critical in helping to loosen biofilm, tartar stain residue and other debris from tooth surfaces which substances are usually entrapped by the micromesh structure of the spent tape and then removed.

In addition to the cleaners and Soft Abrasives™ described above, the coatings loaded onto and into the micromesh structure can also contain various chemotherapeutic ingredients including anti-biofilm and anti-tartar agents as well as active ingredients such as antimicrobials, biofilm attachment altering ingredients such as MICRODENT® and ULTRAMULSION® and anti-tartar ingredients such as the pyrophosphates. All of these can be delivered interproximally and subgingivally by the coated micromesh interproximal devices of the present invention during flossing.

The innovative micromesh interproximal devices of the present invention are designed to replace both:

a. commercial monofilament dental tapes such as Gore's Glide®, J&J's Easy Slide®, Colgate's Total® and Oral-B's Satin® Floss, as well as b. commercial waxed, multifilament dental flosses such as J&J's REACH® Waxed Flosses and REACH® Gentle Gum Care and Ranir's Hi-Tech® Floss.

The broad appeal of micromesh interproximal devices loaded with various coatings to monofilament tape users and to multifilament floss users represents a major advance in interproximal dental devices that promises to:

a. improve overall interproximal cleaning, b. improve the disruption and/or removal of biofilm, tartar stained pellicle, debris, etc., from tooth surfaces, and entrapment and removal of these dislodged substances from between teeth and below the gum line, and c. encourage flossing compliance.

Accordingly, the present invention is directed to shred-resistant, coated, ultra-high molecular weight polyethylene, micromesh interproximal device produced by:

a. fibrillating and slitting stretched polyethylene film having a tensile strength from between about 0.7 GPa and about 5 GPa, wherein said polyethylene has an intrinsic viscosity of from between about 5 and about 50 dl/g, wherein fibrillation as illustrated in FIGS. 1*a* through 1*f* is preferably achieved using rotary fibrillators, wherein the transfer speed of the stretched polyethylene tape is from between about 1 and about 1000 m/min and the rotational line speed of the fibrillator in rotational contact with the polyethylene tape, is from between about 10 and about 3000 m/min, and the fibrillation density is from between about 5% and 90% of the total interproximal device surface, and b. compression, injection and/or contact loading said micromesh polyethylene interproximal device with coatings of high, medium or low melt viscosity mixtures and emulsions containing: cleaners, chemotherapeutic ingredients and Soft Abrasives™ at from between about 10 and about 120 mg/yd.

Advantageously, the micromesh structure of the device is most receptive to the compression injection or contact loading processes and produces a coated interproximal device that remains substantially flake-free while generally readily releasing the coating during flossing.

Advantageously, when the loaded coating contains insoluble Soft Abrasives™ of an appropriate particle size, these abrasives, once released, tend to compliment the micromesh structure during flossing to gently scrub biofilm, tartar and stained pellicle off tooth surfaces. This is further shown in the schematic illustration set out in FIG. 7. This Soft Abrasives™ scrubbing action is readily perceptible and is generally described as "you can feel it working."

The loaded micromesh dental devices of the present invention are a most effective means for delivering chemotherapeutic substances to interproximal and subgingival areas of the oral cavity. The chemotherapeutic substances contained in the coatings loaded onto and into the micromesh dental devices of the present invention can be delivered to specific interproximal and subgingival sites during flossing. This site-specific delivery of localized concentrations of chemotherapeutics is obviously preferred over the use of systemic and/or mouth rinse treatments which impose substantially greater body burdens.

Various chemotherapeutic agents suitable for inclusion in the coatings of the present invention include:

1. anti-tartar substances such as MICRODENT®, ULTRAMULSION®, tetrasodium pyrophosphate (TSPP), tetrapotassium pyrophosphates, sodium hexametaphosphate, etc.;

2. first generation anti-biofilm agents which are antibacterial agents with limited substantivity such as oxygenating compounds, quaternary ammonium compounds, phenolic compounds and plant alkaloids, including:

a. quaternary ammonium compounds such as benzethonium chloride, cetylpyridinium chloride (CPC), b. phenolic compounds such as thymol and phenol, methyl salicylate and other compositions such as benzoic acid and boric acid, c. natural extracts (flavor oils) known to possess antimicrobial properties including eucalyptol, and d. sanguinaria extract, alone or in combination with zinc chloride, or zinc chloride alone, e. triclosan, and f. iodine;

3. second generation agents which are antibacterial agents with substantivity such as chlorhexidine, either free base or as the gluconate or other suitable salt, alexidine, octenidine and stannous fluoride. The treatment of the oral cavity with stannous fluoride or chlorhexidine antimicrobial containing micromesh dental devices are preferred embodiments of the present invention;

4. desensitizing agents, NSAIDs, antibiotics, anti-thrush agents, substances to neutralize candida sp. yeasts, anti-caries agents, antimicrobials, COX-2 agents, etc.;

5. dry mouth relieving agents;
6. NSAIDs including aspirin;
7. Antibiotics including doxycycline, tetracycline and minocycline; and
8. metronidazole.

Examples of saliva-insoluble formula modifiers suitable for contact coating include:
   microcrystalline waxes,
   paraffin wax,
   carnuba, beeswax and other natural waxes,
   animal and vegetable fats and oils, and
   low-melt point, orally suitable polymers and copolymers.

Examples of saliva-soluble formula modifiers include so-called water soluble waxes, including:
   liquid polyethylene glycols,
   solid polyethylene glycols,
   liquid polypropylene glycols,
   solid polypropylene glycols, and
   triacetin.

Examples of low melt temperature, water-soluble polymers, include:
   hydroxyethylcellulose,
   hydroxypropylcellulose,
   carboxy derivatives of cellulose, and
   orally suitable saliva gelling or water-soluble copolymers of various resins.

PREFERRED ASPECTS OF THE INVENTION

According to one preferred aspect of this invention, there is provided an interproximal device formed by fibrillating and slitting an ultra-high molecular weight, stretched, polyethylene tape to produce a micromesh substrate suitable for loading with a saliva-soluble, crystal-free coating comprising cleaners, chemotherapeutic ingredients and Soft Abrasives™ wherein said polyethylene micromesh:
   a. has a tensile strength between from about 0.7 and about 5 GPa, and
   b. has an intrinsic viscosity from between about 5 and about 50 dl/g,
   c. is stretched in a solid state at a temperature lower than the melting point of the polyethylene at a total draw ratio from between about 80 and about 200 fold, and
   d. is fibrillated under conditions where the transfer speed of the stretched polyethylene tape is from between about 1 and about 1000 m/min and the rotational line speed of the fibrillator means in contact with the stretched tape is from between about 10 and about 3000 m/min, to produce fibrillation densities from between about 5% and about 90% of the total device surface.

According to another aspect of this invention, there is provided a micromesh, ultra-high molecular weight, polyethylene interproximal device with various coatings loaded by compression, injection or contact means as described in FIGS. 8 through 13.

Each of these various loading means are used for loading specific coatings into and/or onto the micromesh interproximal devices of the present invention. For example:
(1) compression loading is used to load high melt viscosity mixtures and emulsions as described in Tables 1 through 4;
(2) injection loading is used to load medium melt viscosity mixtures and emulsions as described in Table 5; and
(3) contact loading is used to load low melt viscosity mixtures and emulsions as described in Table 6.

According to another aspect of this invention, there is provided a micromesh interproximal device that is compression loaded with a high melt viscosity emulsion that:
   a. is saliva soluble
   b. is substantially crystal-free
   c. is present at from between about 10 and about 120 mg/yd, and
   d. contains cleaners, Soft Abrasives™ and chemotherapeutic substances.

According to still another aspect of this invention, there is provided a method for producing micromesh, ultra-high molecular weight, polyethylene, interproximal devices which includes:
1. stretching an ultra-high molecular weight, polyethylene film at a total draw ratio between about 80 and about 200 fold
2. fibrillating and slitting said film to produce a micromesh structures such as shown in FIGS. 1a through 1f, and the photographs in Drawings, FIGS. 2 and 5, and
3. compression loading said micromesh device at from between about 10 and about 120 mg/yd with a saliva-soluble, crystal-free, high melt emulsion coating containing surfactants, Soft Abrasives™ and chemotherapeutic substances.

According to a preferred aspect of this invention, there is provided a method for removing biofilm, tartar and stained pellicle from tooth surfaces comprising flossing said surfaces with an interproximal device comprising an ultra-high molecular weight, stretched, polyethylene, micromesh device, compression loaded with a saliva-soluble, crystal-free, high melt emulsion coating at from between about 10 and about 120 mg/yd.

According to a further preferred aspect of this invention, there is provided a method for the site-specific delivery of chemotherapeutic substances to various interproximal and subgingival areas by flossing with a loaded micromesh dental device with a saliva-soluble, crystal-free coating containing one or more chemotherapeutic substances.

According to still another aspect of this invention, there is provided a means for compression loading micromesh, ultra-high molecular weight, polyethylene, interproximal devices with saliva-soluble, crystal-free, high melt emulsion coating compositions containing Soft Abrasives™ that are releasable during flossing and available for complimenting the micromesh structure and its scrubbing action to remove biofilm, tartar and stained pellicle.

According to a further preferred aspect of this invention, there is provided a method and means for treating gingivitis, interproximally and below the gum line, comprising flossing the specific areas of gingival inflammation with a micromesh dental device of the invention, compression loaded with a saliva-soluble, crystal-free coating, high melt emulsion containing chlorhexidine digluconate and Soft Abrasives™. During flossing, the released Soft Abrasives™ in cooperation with the micromesh structure helps remove chlorhexidine stained pellicle from previous chlorhexidine treatments, and the "spent" micromesh device entraps and removes these dislodged staining substances from between teeth and below the gum line.

DETAILED DESCRIPTION OF THE PREFERRED EMBODIMENTS

Particularly preferred micromesh dental devices of the present invention are distinguished from multifilament floss and monofilament tape devices by:

1. their ultra-high molecular weight which translates to exceptional tensile strength and resistance to shredding,
2. their fibrillated construction (with fibrillation densities between 5% and about 90%) which translates to exceptional gentleness combined with the ability to clean biofilm, tartar and stained pellicle from tooth surfaces particularly when combined with certain Soft Abrasives™ during flossing,
3. their saliva-soluble, crystal-free substantive coatings which are substantially free from flaking while containing cleaners, Soft Abrasives™ and chemotherapeutic ingredients that are released in total during flossing and worked into interproximal and subgingival areas. Preferably, the cleaner is added to the coating as an aqueous-free, hot-melt emulsion containing a surfactant as the continuous phase of the emulsion and a coating substance insoluble in the surfactant as the discontinuous phase of the emulsion, and
4. their superior entrapment factor.

Suitable emulsions for purposes of the present invention include those described and claimed in the various MICRO-DENT® and ULTRAMULSION® U.S. Patents including U.S. Pat. Nos. 4,911,927; 4,950,479; 5,032,387; 5,098,711; 5,165,713; 5,538,667; 5,645,841; 5,561,959 and 5,665,374, all of which are hereby incorporated by reference.

Examples of suitable surfactants include:
 sodium lauryl sulfate,
 sodium lauryl sarcosinate,
 polyethylene glycol stearate,
 polyethylene glycol monostearate,
 coconut monoglyceride sulfonates,
 sodium alkyl sulfate,
 sodium alkyl sulfoacetates,
 block copolymers of polyoxyethylene and polyoxybutylene,
 allylpolyglycol ether carboxylates,
 polyethylene derivatives of sorbitan esters,
 propoxylated cetyl alcohol,
 block copolymers comprising a cogeneric mixture of conjugated polyoxypropylene and
  polyoxylethylene compound having as a hydrophobe a polyoxypropylene polymer of at least 1200 molecular weight (these surfactants are generally described as poloxamers; specific examples are described in the Examples below) as Poloxamer 407 and Poloxamer 388,
 soap powder,
 and mixtures thereof.

Examples of suitable coating substances include waxes (both natural and synthetic), silicones, silicone glycol copolymers and polydimethylsiloxanes at molecular weights from between about 1000 cs and several million cs. (Specific examples are described in the Examples below including PDMS 2.5 million and ULTRAMULSION® 10-2.5.)

Micromesh polyethylene tapes suitable for loading with the coatings of the present invention and useful as interproximal devices are available from Integrated Textile Systems, Inc., Monroe, North Carolina, under the trademark Tensylon™. Specific Tensylon™ micromesh polyethylene substrates available include various tapes at various fibrillation densities. Some of these commercial Tensylon tapes are designated as: Fib 42, Fib 53, Fib 70, Fib 200, etc. (These are described further in the photographs set out in FIGS. 2 through 4 and the Examples below.)

The fibrillators used for these Tensylon™ micromesh substrates are of the rotary type fitted with multiple sets of needle-like and tapping screw-like arrangements (see FIGS. 5 and 6) that penetrate the stretched polyethylene tape as it is passed under fibrillators at very high speeds. See FIGS. 1 through 4.

These Tensylon™ tapes are available in various dimensions and denier, including: widths from between about 0.12 and about 0.035 inches, thickness from between about 0.001 and about 0.004 inches and denier from between about 200 and about 600.

Suitable abrasives for use with micromesh devices of the present invention, which are designated by the trademark Soft Abrasives™, include dicalcium phosphate (DCP), sodium hexametaphosphate, pumice, aluminum silicate, silica, glass beads, titanium oxide, rice flour, quartz, novaculite, silicon carbide, alumina zirconia, alumina, polishing alumina, calcined aluminum oxide, silicon and zirconium oxide; all of the foregoing at various crystal forms and particle shapes; various hardness including Rockwell 48-50c at various sieve analysis ranging from U.S. sieve #60 to #270; various specific gravity ranges including 2.65 gm/cc, 3.20 gm/cc, 4.3 gm/cc, 3.6 to 3.9 gm/cc.

These abrasives are preferably added to saliva-soluble coatings at between about 0.25% and about 20% by weight of the micromesh substrate. An alternative method for adding additional abrasive to coated micromesh devices is by means of a dusting process where the coated micromesh device is passed through a chamber charged with abrasive particles in the air, wherein the abrasive particles coat the coated micromesh device as it passes through the dusting chamber.

Suitable abrasives are commercially available from AGSCO Corp., Wheeling, Ill.

The present invention is hereinafter described specifically by way of Examples as detailed in Tables 1 through 6. However, the present invention is by no means limited to these Examples.

In Examples 1 through 30, various ultra-high molecular weight polyethylene films are stretched, slit and fibrillated at various levels of fibrillation as indicated in the tables. These fibrillated micromesh devices are then loaded with various coating compositions as detailed in the various tables.

The various molten coatings described are prepared using a homogenizer and heating the coating mixture in a stainless steel vessel. These coatings can be compression or injection loaded onto the micromesh floss as illustrated in FIGS. 8 through 12 using a range of slub settings for the compression loading such as 0.006 inch and a range of nip roll spacings such as 0.0045 inch.

Coating loads at the 30 to 65 mg/yd range are readily obtained with a wide range of coating compositions.

Illustrative Examples 1 through 4 as set out in Table 1 below describe certain preferred embodiments of the invention.

TABLE 1

| Ex. No. | Polymer Type (Mol. Wt. in intrinsic viscosity dl/g) | Stretched Film Draw Ratio | Stretched Film Tensile Strength (in GPa) | Fibrillation Type as shown in FIGS. 1a–1f (denier) | Fibrillation Density (in %) | Saliva-Soluble, Crystal-Free, High Melt Viscosity Emulsion Coating Compression Load (in mg/yd) | Release Value (in %) | Cleaners (% by wt.) | Soft Abrasives ™ (% by wt.) | Release Value (in %) |
|---|---|---|---|---|---|---|---|---|---|---|
| 1 | ultra-high molec. wt. polyethylene (5) | 80 | 0.7 | FIG. 1a (350) | 40 | 45 | 100 | 30 | 20 | 100 |
| 2 | ultra-high molec. wt. polyethylene (50) | 210 | 5 | FIG. 1c (300) | 90 | 120 | 100 | 40 | 25 | 95 |
| 3 | ultra-high molec. wt. copolymer of ethylene and propylene (20) | 140 | 3.2 | FIG. 1f (400) | 60 | 60 | 100 | 25 | 10 | 98 |
| 4 | ultra-high molec. wt. copolymer of ethylene and butene-1 (25) | 110 | 2 | FIG. 1b (450) | 50 | 20 | 100 | 10 | 40 | 100 |

Illustrative Examples 5 to 8 in Table 2 below describe preferred saliva-soluble, crystal-free, high melt viscosity emulsi loaded onto various micromesh devices similar to those shown in FIGS. 2 and 5 of the Drawings.

TABLE 2

| Ex. No. | Floss Denier | Floss Width (in inches) | Floss Thickness (in inches) | Floss Fibrillation Density (in %) | High Melt Viscosity Emulsion Coating Compression Load (in mg/yd) | Type of surfactant (% by wt.) | Type of silicone (% by wt.) | Type of Soft Abrasive ™ (% by wt.) | Crystal-Free Ingredients (% by wt.) | Release Value (in %) |
|---|---|---|---|---|---|---|---|---|---|---|
| 5 | 350 | .052 | .001 | 50 | 43 | Poloxamer 407 (52) | PDMS 2.5 million (5.7) | DCP (3) | Emsorb 2726 (2) Stearyl alcohol (10) | 98 |
| 6 | 350 | .052 | .001 | 55 | 45 | Poloxamer 407 (52) | PDMS 2.5 million (5.7) | DCP (6) | Emsorb 2726 (3) Stearyl Alcohol (15) | 95 |
| 7 | 500 | .065 | .002 | 20 | 38 | Poloxamer 388 (43) | PDMS 2.5 million (5.7) | Silica (3) | Emsorb 2726 (1) Stearyl Alcohol (14) | 100 |
| 8 | 500 | .065 | .002 | 30 | 40 | Poloxamer 388 (43) | PDMS 2.5 million (8.2) | Calcium Carbonate (8) | Emsorb 2726 (3) Stearyl Alcohol (12) | 100 |

Saliva-soluble, crystal-free, substantially flake-free, high melt viscosity emulsion coatings suitable for the micromesh devices of the invention are set out in Examples 9 through 26 in Table 3 below:

TABLE 3

| Ingredient | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|
| Ultramulsion 10-2.5* | 57.1 | 54.8 | 52.3 | 50.8 | 50.8 | 50.8 | 58.8 | 60.8 | | 60.1 | 55.1 | 51.1 | 60.1 | | 61.1 | 61.1 | 53.1 | 57.1 |
| POLOXAMER 407 | | | | | | | | | 60.1 | | | | | 60.1 | | | | |
| Emsorb 2726 | 12.5 | 7.5 | 12.5 | 9 | 5 | 3 | 3 | 0 | 3 | 3 | 3 | 3 | 3 | 3 | 4 | 3 | 3 | 3 |
| Stearyl Alcohol | 9.2 | 10.5 | 8 | 7 | 11 | 13 | 15 | 16 | 15 | 15 | 15 | 15 | 15 | 15 | 10 | 8 | 15 | 15 |
| Insoluble Saccharin | 1.8 | 1.8 | 1.8 | 1.8 | 1.8 | 1.8 | 1.8 | 1.8 | 1.8 | 1.8 | 1.8 | 1.8 | 1.8 | 1.8 | 1.8 | 1.8 | 1.8 | 1.8 |
| Propyl gallate | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| Spicemint Flavor | 4 | 4 | 4 | 4 | 4 | 4 | 4 | 4 | 5 | 5 | 5 | 5 | 5 | 5 | 5 | 5 | 5 | 5 |
| Vanilla Mint Flavor | 4 | 4 | 4 | 4 | 4 | 4 | 4 | 4 | 5 | 5 | 5 | 5 | 5 | 5 | 5 | 5 | 5 | 5 |

TABLE 3-continued

| Ingredient | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|
| tetrasodium-pyrophosphate | 8 | 14 | 14 | 10 | 10 | 10 | 10 | 10 | 10 |  | 10 | 14 | 4 |  | 6 | 6 | 10 | 6 |
| dicalcium phosphate |  |  |  |  |  |  |  |  |  | 10 |  |  | 6 | 10 |  |  |  |  |
| Microcrystalline Wax ML 445 |  |  | 10 | 10 | 10 | 0 | 0 | 0 | 0 | 5 | 5 |  | 0 | 7 | 10 | 7 | 7 |

TABLE 4

Micromesh Device with saliva-soluble, crystal-free, high melt viscosity emulsion coatings with chemotherapeutic ingredients and Soft Abrasives ™

| | Micromesh Device | | | | Saliva-Soluble, Crystal-Free, High Melt Viscosity Emulsion Coatings | | | |
|---|---|---|---|---|---|---|---|---|
| Ex. No. | Denier | Width (in inches) | Thickness (in inches) | Fibrillation Density (in %) | Compression Load (in mg/yd) | Crystal-Free Ingredients (% by wt.) | Type of Soft Abrasive ™ | Type of Chemotherapeutic Ingredient (% by wt.) | Release Value (in %) |
| 27 | 350 | 0.055 | 0.001 | 40 | 42 | Emsorb 2726 (3) Stearyl alcohol (12) | Dicalcium phosphate | Triclosan (0.6) | 100 |
| 28 | 350 | 0.055 | 0.001 | 60 | 42 | Emsorb 2726 (2) Stearyl alcohol (15) Microwax (7) | Silica, Dicalcium phosphate | Chlorhexidine (0.6) | 100 |
| 29 | 500 | 0.079 | 0.001 | 80 | 58 | Emsorb 2726 (3) Microwax (7) | Calcium carbonate | Metronidazole (0.8) | 95 |
| 30 | 500 | 0.079 | 0.001 | 90 | 61 | Stearyl alcohol (10) Microwax (7) | Silica | Stannous fluoride (4.8) | 100 |

TABLE 5

Micromesh devices injection loaded with medium melt viscosity emulsion or mixture coatings

| | Micromesh Device | | | Medium Melt Viscosity Emulsion or Mixture Coating | |
|---|---|---|---|---|---|
| Ex. No. | Denier | Width (in inches) | Thickness (in inches) | Injection Load (in mg/yd) | Ingredient | Percent by Wt. |
| 31 | 400 | .060 | .001 | 40 | PEG 1450 | 27 |
| | | | | | Microcrystalline Wax | 3 |
| | | | | | Ultramulsion 10-2.5* | 5 |
| | | | | | POLOXAMER 407 | 45 |
| | | | | | Preferred Abrasive System | 10 |
| | | | | | Insoluble Saccharin | 2 |
| | | | | | Flavor and Preservatives | 8 |
| 32 | 350 | .052 | .001 | 52 | PEG 1450 | 20 |
| | | | | | Hydrogenated Vegetable Oil | 10 |
| | | | | | Ultramulsion 10-2.5* | 10 |
| | | | | | POLOXAMER 407 | 40 |
| | | | | | Preferred Abrasive System | 10 |
| | | | | | Insoluble Saccharin | 2 |
| | | | | | Flavor and Preservatives | 8 |
| 33 | 500 | .065 | .002 | 47 | PEG 1450 | 15 |
| | | | | | PEG 600 | 5 |
| | | | | | Ultramulsion 10-2.5* | 10 |
| | | | | | POLOXAMER 338 | 50 |
| | | | | | Carnuba Wax | 5 |
| | | | | | Preferred Abrasive System | 5 |
| | | | | | Insoluble Saccharin | 2 |
| | | | | | Flavor and Preservatives | 8 |

TABLE 5-continued

Micromesh devices injection loaded with medium melt viscosity emulsion or mixture coatings

| | | Micromesh Device | | | Medium Melt Viscosity | |
| --- | --- | --- | --- | --- | --- | --- |
| | | Width | Thickness | Injection Load | Emulsion or Mixture Coating | |
| Ex. No. | Denier | (in inches) | (in inches) | (in mg/yd) | Ingredient | Percent by Wt. |
| 34 | 500 | .065 | .002 | 62 | PEG 4000 | 30 |
| | | | | | Sorbitol | 5 |
| | | | | | hydroxypropylcellulose | 10 |
| | | | | | Ultramulsion 10-2.5* | 10 |
| | | | | | POLOXAMER 407 | 20 |
| | | | | | Preferred Abrasive System | 10 |
| | | | | | Insoluble Saccharin | 2 |
| | | | | | Flavor and Preservatives | 8 |

TABLE 6

Micromesh devices contact loaded with low melt viscosity emulsion or mixture coatings

| | | Micromesh Device | | Contact | Low Melt Viscosity | |
| --- | --- | --- | --- | --- | --- | --- |
| | | Width | Thickness | Coating Load | Emulsion or Mixture Coating | |
| Ex. No. | Denier | (in inches) | (in inches) | (in mg/yd) | Ingredient | Percent by Wt. |
| 35 | 350 | .055 | .001 | 20 | Microcrystalline Wax | 80 |
| | | | | | Hydrogenated Vegetable Oil | 5 |
| | | | | | POLOXAMER 407 | 5 |
| | | | | | PEG 40 sorbitan diisostearate | 5 |
| | | | | | Preferred Abrasive System | 0 |
| | | | | | Insoluble Saccharin | 1 |
| | | | | | Flavor and Preservatives | 4 |
| 36 | 350 | .055 | .001 | 35 | Microcrystalline Wax | 85 |
| | | | | | Hydrozyethyl cellulose | 3 |
| | | | | | POLOXAMER 407 | 2 |
| | | | | | PEG 40 sorbitan diisostearate | 5 |
| | | | | | Preferred Abrasive System | 0 |
| | | | | | Insoluble Saccharin | 1 |
| | | | | | Flavor and Preservatives | 4 |
| 37 | 350 | .055 | .001 | 18 | Microcrystaline Wax | 82 |
| | | | | | Hydrogenated Vegetable Oil | 3 |
| | | | | | POLOXAMER 407 | 0 |
| | | | | | PEG 40 sorbitan diisostearate | 5 |
| | | | | | Preferred Abrasive System | 5 |
| | | | | | Insoluble Saccharin | 1 |
| | | | | | Flavor and Preservatives | 4 |
| 38 | 500 | .079 | .001 | 18 | Microcrystaline Wax | 85 |
| | | | | | PEG 40 sorbitan diisostearate | 5 |
| | | | | | Preferred Abrasive System | 2 |
| | | | | | Insoluble Saccharin | 2 |
| | | | | | Flavor and Preservatives | 6 |

EXAMPLE 39

A spool of micromesh tape, 460 denier, 1.7 thousandths inch thickness, constructed of ultra high molecular weight polyethylene, with a relative fibrillation of 42, was put on a dispensing creel under a controlled tension of 150 grams. The tape was routed into an applicator tank under four splaying bars.

The coating formula consists of 57.1 percent ULTRAMULSION® 10/2.5 (90 percent poloxamer 407 and 10 percent polydimethylsiloxane, 2.5 million centistokes); 7 percent microcrystaline wax 445; 3.0 percent PEG 40 sorbitan diisostearate; 15 percent stearyl alcohol; 1.8 percent insoluble saccharin; 0.1 percent propyl gallate; 10 percent flavor; and 6.0 percent dicalcium phosphate dihydrate.

The ingredients were heated at 85° C. and stirred vigorously until homogeneous and added to the applicator tank until the four bars were covered.

The micromesh tape was threaded under four splaying bars and up through a slub gap of 0.005 inches and between two compression rollers heated to 65° C. gapped at 0.005 inches and heated at 65° C. The tape was then threaded through a 40 foot long cooling tunnel at 7° C. and on to Lessona 959 take-up winders. The line speed was increased to 1.5 yards per second to produce 2210 yards.

A sample of tape was measured for load level and gave 41.4 mg/yd.

EXAMPLE 40

A spool of micromesh tape, 460 denier, 1.7 thousandths inch thickness, constructed of ultra high molecular weight polyethylene, with a relative fibrillation of 70, was put on a dispensing creel under a controlled tension of 150 grams. The tape was routed into an applicator tank under four splaying bars.

The coating formula consists of 57.1 percent ULTRAM-ULSION® 10/2.5 (90 percent poloxamer 407 and 10 percent polydimethylsiloxane, 2.5 million centistokes); 7 percent microcrystalline wax 445; 3.0 percent PEG 40 sorbitan diisostearate; 15 percent stearyl alcohol; 1.8 percent insoluble saccharin; 0.1 percent propyl gallate; 10 percent flavor; and 6.0 percent dicalcium phosphate dihydrate.

The ingredients were heated at 85° C. and stirred vigorously until homogeneous and added to the applicator tank until the four bars were covered.

The micromesh tape was threaded under four splaying bars and up through a slub gap of 0.005 inches and between two compression rollers gapped at 0.005 inches and heated at 85° C. The tape was then threaded through a 40 foot long cooling tunnel at 7° C. and on to Lessona 959 take-up winders. The line speed was increased to 1.5 yards per second to produce 2210 yards.

A sample of tape was measured for load level and gave 51.3 mg/yd.

EXAMPLE 41

A spool of micromesh tape, 460 denier, 1.7 thousandths inch thickness, constructed of ultra high molecular weight polyethylene, with a relative fibrillation of 200, was put on a dispensing creel under a controlled tension of 150 grams. The tape was routed into an applicator tank under four splaying bars.

The coating formula consists of 57.1 percent ULTRAM-ULSION® 10/2.5 (90 percent poloxamer 407 and 10 percent polydimethylsiloxane, 2.5 million centistokes); 7 percent microcrystalline wax 445; 3.0 percent PEG 40 sorbitan diisostearate; 15 percent stearyl alcohol; 1.8 percent insoluble saccharin; 0.1 percent propyl gallate; 10 percent flavor; and 6.0 percent dicalcium phosphate dihydrate.

The ingredients were heated at 85° C. and stirred vigorously until homogeneous and added to the applicator tank until the four bars were covered.

The micromesh tape was threaded under four splaying bars and up through a slub gap of 0.005 inches and between two compression rollers gapped at 0.005 inches and heated at 85° C. The tape was then threaded through a 40 foot long cooling tunnel at 7° C. and on to Lessona 959 take-up winders. The line speed was increased to 1.5 yards per second to produce 2210 yards.

A sample of tape was measured for load level and gave 56.2 mg/yd.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

The invention claimed is:

1. An ultra-high molecular weight polyethylene film: having a tensile strength from between about 0.7 GPa and about 5 GPa where said polyethylene has an intrinsic viscosity from between about 5 and about 50 db/g; that is stretched, fibrillated and slit into a micromesh tape suitable for use as an interproximal device having:
   a fibrillation density from between about 5% and about 90% of the total tape surface,
   a width from between about 0.035 and about 0.12 inches,
   a thickness from between about 0.001 and about 0.004 inches, and
   a denier from between about 200 and about 600;
   wherein said micromesh interproximal device is coated with an oral care substance at from between about 10 and about 120 mg/yd and which, during flossing, releases substantial amounts of said coating while demonstrating ultra shred resistance and an entrapment factor of at least about two;
   and where said oral care substance is selected from the group consisting of hedonic agents, cleaners, chemotherapeutic agents, abrasives, and mixtures thereof.

2. The ultra-high molecular weight polyethylene film according to claim 1, wherein said stretching is achieved by a drawing means, wherein the total draw ratio is from between about 80- and about 200-fold.

3. The ultra-high molecular weight polyethylene film according to claim 1, wherein said fibrillating is achieved by fibrillating devices selected from the group consisting of a tapping screw-like fibrillator and a file-like fibrillator.

4. The coated ultra-high molecular weight polyethylene micromesh interproximal device according to claim 1, wherein said coating with an oral care substances, is achieved by a coating means selected from the group consisting of: compression loading, injection loading and contact loading, and combinations thereof.

5. The coated ultra-high molecular weight polyethylene micromesh interproximal device according to claim 1, wherein said oral care coating substance further comprises a composition selected from the group consisting of: high melt viscosity mixtures, high melt viscosity emulsions, medium melt viscosity mixtures, medium melt viscosity emulsions, low melt viscosity mixtures and low melt viscosity emulsions, and combinations thereof.

6. The coated ultra-high molecular weight polyethylene micromesh interproximal devices according to claim 5, wherein said high melt viscosity mixtures and high melt viscosity emulsions are compression loaded into said micromesh at levels from between about 10 and about 120 mg/yd and said high melt viscosity mixtures and emulsions comprise saliva soluble, substantially crystal-free coatings containing oral care substances selected from the group consisting of hedonic agents, cleaners, chemotherapeutic agents, abrasives, and mixtures thereof.

7. The coated ultra-high molecular weight polyethylene micromesh interproximal devices according to claim 5, wherein said medium melt viscosity mixtures and medium melt viscosity emulsions are injection loaded into said micromesh at levels from between about 10 and about 120 mg/yd and said medium melt viscosity mixtures and emulsions comprise coatings selected from the group consisting of:
   (a) saliva soluble, substantially crystal-free coatings containing oral care substances selected from the group consisting of hedonic agents, cleaners, chemotherapeutic agents, abrasives, and mixtures thereof;
   (b) saliva gelling, slowly soluble mixtures containing oral care substances selected from the group consisting of hedonic agents, cleaners, chemotherapeutic agents, abrasives and mixtures thereof; and mixtures of (a) and (b).

8. The coated ultra-high molecular weight polyethylene micromesh interproximal devices according to claim 5, wherein said low melt viscosity emulsions are contact loaded onto said micromesh at levels from between about 10 and 120 mg/yd and said low melt viscosity mixtures and emulsions comprise coatings selected from the group consisting of:
(a) saliva soluble coatings
(b) saliva insoluble coatings, and
(c) mixtures of (a) and (b).

9. An ultra-high molecular weight polyethylene micromesh tape suitable for use as an interproximal device, wherein the dispensing means for said tape is selected from the group consisting of bobbin based dispensers and single dose dispensers.

10. A shred-resistant, ultra-high molecular weight polyethylene, micromesh interproximal device produced by fibrillating stretched polyethylene tape having a tensile strength from between about 0.7 GPa and about 5 GPa, where said polyethylene has an intrinsic viscosity of from between about 5 and about 50 dl/g; and wherein said device is coated with a saliva-soluble, substantially crystal-free coating at a load from between about 10 and about 120 mg/yd.

11. A method of manufacturing the micromesh interproximal device of claim 1, wherein said stretched polyethylene tape is run at a transfer speed from between about 1 and about 1000 m/min and said fibrillating is carried out simultaneously with a rotary fibrillator positioned in fibrillating contact with said polyethylene tape and run at a rotational line speed from between about 10 and about 3000 m/min and said coating is carried out at between about 1 and about 5 yards per second.

12. A method of manufacturing the micromesh interproximal device of claim 11, wherein said fibrillated tape is compression loaded by passing said fibrillated tape through a coating chamber and thereafter passing said coated fibrillated tape between juxtapositioned heated rollers under compression conditions.

13. A micromesh interproximal device according to claim 5, wherein said oral care coating substance contains cleaners selected from the group consisting of:
sodium lauryl sulfate,
sodium lauryl sarcosinate,
polyethylene glycol stearate,
polyethylene glycol monostearate,
coconut monoglyceride sulfonates,
sodium alkyl sulfate,
sodium alkyl sulfoacetates,
block copolymers of polyoxyethylene and polyoxybutylene,
allylpolyglycol ether carboxylates,
polyethylene derivatives of sorbitan esters,
propoxylated cetyl alcohol,
block copolymers comprising a cogeneric mixture of conjugated polyoxypropylene and polyoxylethylene compound having as a hydrophobe a polyoxypropylene polymer of at least 1200 molecular weight,
soap powder,
and mixtures thereof.

14. A micromesh interproximal device according to claim 5, wherein said oral care coating substance contains Formula Modifiers selected from the group consisting of:
saliva-insoluble formula modifiers, including:
microcrystalline waxes
paraffin wax
carnuba, beeswax and other natural waxes
animal and vegetable fats and oils
low-melt point, orally suitable polymers and copolymers;
saliva-soluble formula modifiers include so-called water soluble waxes, including:
liquid polyethylene glycols
solid polyethylene glycols
liquid polypropylene glycols
solid polypropylene glycols,
triacetin, and
low melt temperature, water-soluble polymers, including:
hydroxyethylcellulose
hydroxypropylcellulose
carboxy derivatives of cellulose and
orally suitable saliva gelling or water-soluble copolymers of various resins.

15. A micromesh interproximal device according to claim 5, wherein said oral care coating substance contains chemotherapeutic ingredients selected from the group consisting of:
anti-tartar substances, an emulsion of polydimethyl siloxane and polyoxypropylene-polyoxyethylene block copolymers, a high shear mixture of high molecular weight block copolymers of ethylene oxide and propylene oxide with high viscosity polydimethylsiloxane polymers, tetrasodium pyrophosphate (TSPP), tetrapotassium pyrophosphates, and mixtures thereof;
first generation anti-biofilm agents, oxygenating compounds, quaternary ammonium compounds, phenolic compounds and plant alkaloids selected from the group consisting of:
benzethonium chloride and cetylpyridinium chloride,
thymol and eucalyptol in a mixture of methyl salicylate, benzoic acid and boric acid and phenol,
flavor oils,
sanguinaria extract with zinc chloride, and
triclosan;
(3) second generation anti-biofilm agents, chlorhexidine, alexidine, octenidine and stannous fluoride;
(4) desensitizing agents, NSAIDs, antibiotics, anti-thrush agents, anti-caries agents, antimicrobials, COX-2 agents;
(5) dry mouth relieving agents;
(6) NSAIDs;
(7) antibiotics; and
mixtures thereof.

16. A micromesh interproximal device according to claim 5, wherein said oral care coating substance contains abrasives selected from the group consisting of:
dicalcium phosphate (DCP),
pumice,
aluminum silicate,
silica,
glass beads,
titanium oxide,
rice flour,
sodium hexametaphosphate,
quartz,
novaculite,
silicon carbide,
alumina zirconia,
alumina,
polishing alumina,
calcined aluminum oxide,
silicon zirconium oxide, and
mixtures thereof.

17. A micromesh interproximal device according to claim 1, where said micromesh structure is selected from the group of structures illustrated in FIGS. 1a through 1f and combinations thereof.

18. A micromesh interproximal device according to claim 6, wherein the additive responsible for maintaining said coating substantially crystal-free and free from substantial flaking is an aliphatic long chain, fatty alcohol selected from the group consisting of:

| | | |
|---|---|---|
| 1-decanol | 1-heptadecanol | 1-pentacosanol |
| 1-undecanol | 1-octadecanol | 1-hexacosanol |
| 1-dodecanol | 1-nonadecanol | 1-heptacosanol |
| 1-tetradecanol | 1-eicosanol | 1-octacosanol |
| 1-pentadecanol | 1-heneicosanol | 1-nonacosanol |
| 1-hexadecanol | 1-tricosanol | 1-triacosanol |
| 1-tetracosanol, and mixtures thereof. | | |

19. A micromesh interproximal device according to claim 6, wherein the additive responsible for maintaining said coating crystal-free is a liquid surfactant having the general formula:

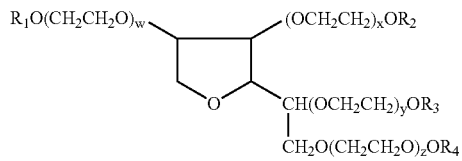

wherein $R_1$, $R_2$, $R_3$, $R_4$ are H or aliphatic acyl groups having from between 10 and 30 carbon atoms, and the sum of w, x, y, and z is from between 20 and 80.

20. A method of cleaning interproximal and subgingival areas of the oral cavity comprising regularly flossing with a shred-resistant, ultra-high molecular weight polyethylene micromesh interproximal device produced by fibrillating stretched polyethylene tape having a tensile strength from between about 0.7 GPa and about 5 GPa, where said polyethylene has an intrinsic viscosity of from between about 5 and about 50 dl/g; and wherein said device is coated with an oral care substance at a load from between about 10 and about 120 mg/yd.

21. A method for treating interproximal and subgingival areas of the oral cavity with chlorhexidine comprising regularly flossing with a micromesh interproximal device compression loaded with a saliva-soluble, crystal-free coating containing abrasives and between about 0.2 and about 2.0 mg/yd of chlorhexidine.

22. A method for treating interproximal and subgingival areas of the oral cavity with stannous fluoride, comprising regularly flossing with a micromesh interproximal device compression loaded with a saliva-soluble, crystal-free coating containing abrasives and between about 1 and about 3 of stannous fluoride.

* * * * *